(12) United States Patent
Yacyshyn et al.

(10) Patent No.: US 11,199,534 B2
(45) Date of Patent: Dec. 14, 2021

(54) PROCESS AND SYSTEM FOR PREDICTING RESPONDERS AND NON-RESPONDERS TO MESALAMINE TREATMENT OF ULCERATIVE COLITIS

(71) Applicants: Bruce Yacyshyn, Cincinnati, OH (US); Mary E. Yacyshyn, Cincinnati, OH (US)

(72) Inventors: Bruce Yacyshyn, Cincinnati, OH (US); Mary E. Yacyshyn, Cincinnati, OH (US)

( * ) Notice: Subject to any disclaimer, the term of this patent is extended or adjusted under 35 U.S.C. 154(b) by 191 days.

(21) Appl. No.: 16/369,242

(22) Filed: Mar. 29, 2019

(65) Prior Publication Data

US 2019/0242872 A1    Aug. 8, 2019

Related U.S. Application Data

(62) Division of application No. 15/068,981, filed on Mar. 14, 2016, now Pat. No. 10,295,527.

(51) Int. Cl.
*G01N 33/49* (2006.01)
*A61K 31/196* (2006.01)
*A61K 31/606* (2006.01)

(52) U.S. Cl.
CPC ......... *G01N 33/492* (2013.01); *A61K 31/196* (2013.01); *A61K 31/606* (2013.01); *G01N 2800/065* (2013.01); *G01N 2800/52* (2013.01); *Y02A 50/30* (2018.01)

(58) Field of Classification Search
None
See application file for complete search history.

(56) References Cited

U.S. PATENT DOCUMENTS

| | | |
|---|---|---|
| 7,923,544 B2 | 4/2011 | Garris |
| 8,008,036 B2 | 8/2011 | Fallon |
| 2005/0101568 A1 | 5/2005 | Kaila |
| 2006/0063162 A1 | 3/2006 | Deng |

(Continued)

FOREIGN PATENT DOCUMENTS

| | | |
|---|---|---|
| CN | 103149371 | 12/2015 |
| WO | WO2007047207 | 4/2007 |

(Continued)

OTHER PUBLICATIONS

International Search Report for Int App. No. PCT/US2019/047231, related to instant application and Written Opinion Of Int. Searching Authority dated Nov. 19, 2019.

(Continued)

*Primary Examiner* — Erin M. Bowers
(74) *Attorney, Agent, or Firm* — Mark F. Smith; Smith Brandenburg Ltd.

(57) ABSTRACT

A process and system directed to a more effective, individual based treatment regimen which is built on clinical identified target biomarkers associated with gender differential responses to mesalamine, and includes one or more panels of target biomarkers that distinguishes mesalamine response differences between genders and determines the efficacy of mesalamine for patients being treated for various UC conditions and effectively identifies and validates novel drug targets for new UC therapeutics, new diagnostics and diagnostics standards for UC therapeutic strategies.

6 Claims, 20 Drawing Sheets

(56) References Cited

U.S. PATENT DOCUMENTS

| | | |
|---|---|---|
| 2007/0020660 A1 | 1/2007 | Burczynski |
| 2007/0087440 A1 | 4/2007 | Axford |
| 2007/0155772 A1 | 7/2007 | Ise |
| 2007/0178078 A1 | 8/2007 | Knoo |
| 2008/0107650 A1 | 5/2008 | Tartaglia et al. |
| 2008/0274118 A1 | 11/2008 | Aukerman |
| 2009/0069564 A1 | 3/2009 | Kaila |
| 2009/0117589 A1 | 5/2009 | Southern |
| 2009/0196927 A1 | 6/2009 | Panitch |
| 2009/0258848 A1 | 10/2009 | Chakravarti |
| 2009/0299767 A1 | 12/2009 | Michon et al. |
| 2009/0312376 A1 | 12/2009 | Rubio Royo |
| 2010/0075891 A1 | 3/2010 | Ayalon-Soffer |
| 2010/0093552 A1 | 4/2010 | Panja |
| 2010/0130367 A1 | 5/2010 | Murthy |
| 2010/0152062 A1 | 6/2010 | Harris |
| 2010/0203522 A1 | 8/2010 | Lee |
| 2010/0255508 A1 | 10/2010 | Gelzleichter |
| 2010/0255513 A1 | 10/2010 | Denson |
| 2010/0267037 A1 | 10/2010 | Westbrook |
| 2010/0279275 A1 | 11/2010 | Panja |
| 2011/0027771 A1 | 2/2011 | Deng |
| 2011/0110924 A1 | 5/2011 | Lazar et al. |
| 2011/0117111 A1 | 5/2011 | Kwon |
| 2011/0003289 A1 | 6/2011 | Salk |
| 2011/0251101 A1 | 10/2011 | Li et al. |
| 2013/0225439 A1 | 8/2013 | Nestec |
| 2013/0303391 A1 | 11/2013 | Li et al. |
| 2017/0261492 A1 | 9/2017 | Yacyshyn |

FOREIGN PATENT DOCUMENTS

| | | | |
|---|---|---|---|
| WO | WO2007131575 A1 | | 11/2007 |
| WO | WO2008043725 A1 | | 4/2008 |
| WO | WO2008147562 A2 | | 12/2008 |
| WO | WO2008153924 A2 | | 12/2008 |
| WO | WO2009036099 A1 | | 3/2009 |
| WO | WO2009046168 A1 | | 4/2009 |
| WO | WO2009037572 A2 | | 6/2009 |
| WO | WO2009120877 A2 | | 10/2009 |
| WO | WO2010029578 | | 3/2010 |
| WO | WO2010062663 | | 3/2010 |
| WO | WO2010056337 | | 5/2010 |
| WO | WO2010073266 | | 7/2010 |
| WO | WO2010085658 | | 7/2010 |
| WO | WO2010147714 A1 | | 12/2010 |
| WO | WO2011033524 A2 | | 3/2011 |
| WO | WO2011034597 A1 | | 3/2011 |
| WO | WO2012037199 | | 3/2012 |
| WO | WO2013059732 | | 4/2013 |
| WO | WO2014104305 | | 3/2014 |
| WO | WO2014182689 | | 11/2014 |
| WO | WO 2015/067913 | * | 5/2015 |
| WO | WO2015067913 | | 5/2015 |

OTHER PUBLICATIONS

Supplementary European Search Report for related European Patent Application EP17767238.1 (PCT/US2017/022013) dated Nov. 11, 2019.

Notificaation of Transmittal of International Preliminary Report On Patentability (including Report), corresponding PCT application No. PCT/US2019/047231 dated May 27, 2020.

International Search report and Written Opinion, Int. App. No. PCT/US2017/022013, Filing Date Mar. 13, 2017.

Goral et al., "Antibodies to 70 kD and 90 kD heat shock proteins are associated with graft-versus-host dieses in peripheral blood stem cell transplant recipients," Clinical & Experimental Immunology, Mar. 31, 2002, vol. 127, No. 3, pp. 553-559.

Krouskou et al., "Apolipoprotein A-I inhibits experimental colitis and colitis-propelled carcinogenesis", Oncogene, Aug. 17, 2015, vol. 35, No. 19, pp. 2496-2505.

Melgar et al., Local production of chemokines and prostaglandin E2 in the acute, chronic and recovery phase of murine experimental colitis, Cytokine, Nov. 7, 2006, vol. 35, Nos. 5-6, pp. 275-283.

Carter et al.. Functional correlates of the interleukin-1 receptor antagonist gene polymorphism in the colonic mucosa in ulcerative colitis,: Genes and Immunity, Jan. 31, 2014, vol. 5, No. 1, pp. 8-15.

Karagozian et al., "The role of mesalamine in the treatment of ulcerative colitis," Tharapeutics and Clinical Risk Mgt, 2007:3(5) 893-903.

AGA Abstracts, Su1187, 2015 SU1187, p. S-425.

* cited by examiner

FIG. 3

Specific Biomarker Panels to be run based on gender and location

| Male & Female Pan/Extensive colitis FIRST PANEL - 112 | | | |
|---|---|---|---|
| Gene name | Analyte full name | Gene name | Analyte full name |
| GSTM1 | Glutathione S-Transferase mu 1 | RETN | Resistin |
| IL13 | Interleukin 13 | | AutoAb to Histone H4 |
| Female Left- Sided Colitis SECOND PANEL - 116 | | Male Left- Sided Colitis THIRD PANEL - 120 | |
| Gene name | Analyte full name | Gene name | Protein name |
| | Antibody to L. donovani | APOA1 | Apolipoprotein A-1 |
| | Antibody to HTLCV1/2 | PRL | Prolactin |
| | AutoAb to HSP90 alpha | IgA | Immunoglobuilin A |
| | | | AutoAb to HSP71 |
| Female Proctosigmoidtis FOURTH PANEL - 124 | | Male Proctosigmoiditis FIFTH PANEL - 128 | |
| Gene name | Analyte full name | Gene name | Protein name |
| CCL22 | MDC or Macrophage – derived chemokine | ILRN | IL 1 receptor antagonist |
| | Antibody to Cholera Toxin | CD40 L | CD40 ligand |

TABLE 1
MALE/FEMALE PAN/EXTENSIVE COLITIS
UNIVARIATE ANALYTES USED FOR MULTIVARIATE MODELING

| Gene | Full Name | P value | Estimate | T value | Succeed or Fail |
|---|---|---|---|---|---|
| Protein | | | | | |
| GSTM1[1] | Glutathione S-Transferase mu 1 | 0.059 | -1.128 | -1.968 | Succeed |
| FABP | Fatty Acid Binding protein | 0.183 | -0.271 | -1.366 | Succeed |
| AFP | Alpha-fetoprotein | 0.186 | -0.328 | -1.355 | Succeed |
| IL7 | Interleukin 7 | 0.020 | 0.045 | 2.471 | Fail |
| SERPINA7 | Thyroxine binding globulin | 0.035 | 0.051 | 2.212 | Fail |
| RETN | Resistin | 0.047 | 0.446 | 2.080 | Fail |
| MPO | Myeloperoxidase | 0.049 | 0.002 | 2.061 | Fail |
| IL13 | Interleukin 13 | 0.054 | 0.049 | 2.017 | Fail |
| SERPINA1 | Alpha-1 antitrypsin | 0.055 | 1.231 | 2.004 | Fail |
| F7 | Coagulation Factor VII | 0.066 | 0.007 | 1.919 | Fail |
| ASP_C3a_des_arg | Cleavage product of complement component C3 activation | 0.072 | 0.001 | 1.870 | Fail |
| Testosterone | | 0.082 | 0.374 | 1.807 | Fail |
| B2M | Beta 2 microglobulin | 0.105 | 1.545 | 1.678 | Fail |
| S100A12 | S100 Calcium binding protein A12 (ENRAGE) | 0.110 | 0.018 | 1.654 | Fail |
| MMP3 | Matrix metallopeptidase 3 | 0.119 | 0.097 | 1.611 | Fail |
| IL3 | Interleukin 3 | 0.131 | 7.372 | 1.556 | Fail |
| C3 | Complement component C3 | 0.135 | 1.778 | 1.541 | Fail |
| APCS | Serum Amyloid P | 0.154 | 0.082 | 1.466 | Fail |
| Progesterone | | 0.157 | 0.194 | 1.454 | Fail |
| VCAM1 | Vascular cellular adhesion molecule 1 | 0.162 | 0.003 | 1.436 | Fail |
| SHBG | Sex hormone binding globulin | 0.163 | 0.026 | 1.434 | Fail |
| CXCL8 | Interleukin 8 | 0.182 | 0.029 | 1.368 | Fail |
| MUC16 | Mucin 16 (CEA 125) | 0.191 | 0.073 | 1.340 | Fail |
| Antibody to infectious agent | | | | | |
| Hep B surface Ad | Ab to Hepatitis B surface antigen subtype Ad | 0.115 | -0.380 | -1.627 | Succeed |
| L.donovani | Ab to Leishmania donovani | 0.062 | 1.254 | 1.942 | Fail |
| Polio virus | Ab to Polio virus | 0.068 | 1.941 | 1.900 | Fail |
| CMV | Cytomegalovirus | 0.092 | 0.089 | 1.744 | Fail |
| Tetanus Toxoid | Ab to tetanus toxoid | 0.114 | 0.014 | 1.634 | Fail |
| Lyme | Ab to lyme disease | 0.131 | 0.049 | 1.558 | Fail |
| Rubeola | Ab to Rubeola | 0.162 | 0.435 | 1.436 | Fail |

[1] Bolded text represents statistically significant analytes associated with multivariate model and panel

FIG. 4B

TABLE 1(Continued)
MALE/FEMALE PAN/EXTENSIVE COLITIS
UNIVARIATE ANALYTES USED FOR MULTIVARIATE MODELING

| Gene | Full Name | P value | Estimate | T value | Succeed or Fail |
|---|---|---|---|---|---|
| | | Autoantibody | | | |
| COL2A1 | AutoAb to collagen type II | 0.181 | -0.596 | -1.373 | Succeed |
| H2A | AutoAb to Histone 2a | 0.042 | 0.781 | 2.135 | Fail |
| INS | AutoAb to Insulin | 0.070 | 1.310 | 1.887 | Fail |
| H4 | AutoAb to Histone 4 | 0.073 | 1.463 | 1.863 | Fail |
| GAD2 | AutoAb to Pancreatic islet cell glutamate decarboxylase | 0.160 | 1.232 | 1.444 | Fail |
| SSB | AutoAb to Sjogren Syndrome antigen B | 0.171 | 1.182 | 1.405 | Fail |

FIG. 5

TABLE 2

DESCRIPTIVE RANGES OF LOCATION AND GENDER SPECIFIC TARGET BIOMARKERS

| Location | Gender | Serological Markers | Unit | Mean | Std Error | Range | N total |
|---|---|---|---|---|---|---|---|
| Proctosigmoidtis | Male | IL1RN | pg/ml | 153.4208 | 11.4008 | 12.65-562 | 149 |
| | | CD40L | ng/ml | 1.6559 | 0.1097 | .0065-7.2 | 149 |
| Proctosigmoidtis | Female | | | | | | |
| | | CCL22 | pg/ml | 578.799 | 20.3739 | 58-1300 | 110 |
| | | Antibody to Cholera toxin | MFI ratio | 3.7836 | 0.0639 | 2.4-6.0 | 110 |
| Left-Sided | Male | | | | | | |
| | | HSP 71 autoantibody | MFI ratio | 3.0981 | 0.0855 | 1.6-7.1 | 106 |
| | | IgA | mg/ml | 3.6019 | 0.1748 | 0.55-9.4 | 106 |
| | | APOA1 | mg/ml | 0.3054 | 0.0128 | 0.13-0.91 | 106 |
| | | PRL | ng/ml | 2.3446 | 0.2313 | 0.18-16.9 | 106 |
| Left-Sided | Female | | | | | | |
| | | Antibody to L. donovani | MFI ratio | 3.233 | 0.0767 | 2.0-5.5 | 78 |
| | | Antibody to HTCLV 1/2 | MFI ratio | 4.6069 | 0.5432 | 2.2-36.42 | 78 |
| | | HSP90α autoantibody | MFI ratio | 8.4071 | 0.3094 | 2.8-15.25 | 78 |
| Extensive/Pancolitis MODEL 1 | Male/Female | | | | | | |
| | | GSTM1 | ng/ml | 1.2863 | 0.0705 | 0.15-1.7 | 76 |
| | | IL13 | pg/ml | 65.6357 | 3.0702 | 13.7-154.0 | 76 |
| | | Histone H2a autoantibody | MFI ratio | 4.4802 | 0.1263 | 2.7-8.0 | 76 |
| MODEL 2 | | Histone H2a autoantibody | MFI ratio | 4.4802 | 0.1263 | 2.7-8.0 | 76 |
| | | RETN | ng/ml | 4.6947 | 0.2891 | 1.4-13.6 | 76 |

FIG. 6

TABLE 3

PREDICTIVE MODELS FOR LOCATION AND GENDER

| Location | Gender | Effect Increment | Serological Markers | Estimate | Std. Error | p-value | Risk Ratio |
|---|---|---|---|---|---|---|---|
| Proctosigmoidtis AUC=.7188 | Male | 100pg/ml | IL1RN | .2844 | .0777 | .0004 | 1.3289 |
| | | 1ng/ml | CD40L | -.6412 | .1915 | .0010 | .5266 |
| | | NA | Intercept | -1.2293 | .2105 | <.0001 | NA |
| Proctosigmoidtis AUC=.7653 | Female | 100pg/ml | CCL22 | .2602 | .0640 | <.0001 | 1.2971 |
| | | .5 MFI ratio unit | Antibody to Cholera toxin | -.5882 | .2142 | .0071 | .5553 |
| | | NA | Intercept | .6750 | 1.4511 | .6428 | NA |
| Left-Sided AUC=.7462 | Male | 1 MFI ratio unit | HSP 71 autoantibody | .3800 | .1479 | .0116 | 1.4623 |
| | | 1 mg/ml | IgA | .1800 | .0789 | .0196 | 1.1973 |
| | | .1mg/ml | APOA1 | -.4925 | .2443 | .0465 | .6111 |
| | | 1 ng/ml | PRL | .1104 | .0509 | .0324 | 1.1167 |
| | | NA | Intercept | -2.3904 | .7046 | .001 | NA |
| Left-Sided AUC=.8546 | Female | 1 MFI ratio unit | Antibody to L. donovani | 1.2037 | .4226 | .0057 | 3.3325 |
| | | 1 MFI ratio unit | Antibody to HTCLV 1/2 | -.8790 | .3247 | .0084 | .4152 |
| | | 1 MFI ratio unit | HSP90α autoantibody | .2544 | .1096 | .0230 | 1.2897 |
| | | 4.8 vs 2.4 g/day | Dose | -1.1354 | .4337 | .0107 | .3213 |
| | | NA | Intercept | -4.385 | 1.9263 | .0270 | NA |
| Extensive/ Pancolitis | Male/ Female | | | | | | |
| MODEL 1 AUC=.8554 | | 1ng/ml | GSTM1 | -1.1553 | .4074 | .0059 | .3150 |
| | | 1pg/ml | IL13 | .1734 | .0741 | .0221 | 1.1893 |
| | | 1 MFI ratio unit | Histone H2a autoantibody | .4988 | .2539 | .0533 | 1.6467 |
| | | NA | Intercept | -3.7842 | 1.4528 | .0112 | NA |
| MODEL 2 AUC=.7883 | | 1 MFI ratio unit | Histone H2a autoantibody | .4001 | .1222 | .0016 | 1.4920 |
| | | 1ng/ml | RETN | .1296 | .0550 | .0212 | 1.1384 |
| | | | Intercept | -4.0207 | .8759 | <.0001 | NA |

FIG. 7

TABLE 4
FEMALE LEFT – SIDED COLITIS
UNIVARIATE ANALYTES USED FOR MULTIVARIATE MODELING

| Gene | Full Name | P value | Estimate | T value | Succeed or Fail |
|---|---|---|---|---|---|
| Protein | | | | | |
| Progesterone | | 0.068 | -0.156 | -1.847 | Succeed |
| ACE | Angiotensin 1 converting enzyme | 0.161 | -0.01 | -1.416 | Succeed |
| CKMB | Creatine kinase (M muscle) or (B brain) | 0.092 | 3.418 | 1.709 | Fail |
| CCL4 | Mip1 beta | 0.092 | 0.003 | 1.707 | Fail |
| CALCA | Calcitonin | 0.116 | 0.162 | 1.589 | Fail |
| CCL5 | RANTES | 0.148 | 0.021 | 1.463 | Fail |
| VEGF | Vascular endothelial growth factor | 0.185 | 0.0005 | 1.338 | Fail |
| IL7 | Interleukin 7 | 0.189 | 0.008 | 1.326 | Fail |
| Antibody to infectious agent | | | | | |
| T. pallidum 15Kd | Ab to Treponema pallidum recombinant 15Kd protein | 0.078 | -0.096 | -1.788 | Succeed |
| HTLCV1/2 | Ab to Human T cell lymphotrophic virus 1/2 | 0.088 | -0.799 | -1.728 | Succeed |
| HSV 1/2 | Herpes Simplex virus 1/2 | 0.134 | -0.043 | -1.515 | Succeed |
| Hep C NS3 | Ab to Hepatitis C non-structural protein 3 | 0.136 | -0.808 | -1.505 | Succeed |
| Cholera Toxin | Ab to Cholera Toxin | 0.147 | -0.729 | -1.464 | Succeed |
| Hep E orf2 6KD | Ab to Hepatitis E open reading frame 2 (major capsid protein) 6Kd | 0.179 | -0.877 | -1.356 | Succeed |
| L.donovani | Ab to Leishmania donovani | 0.087 | 0.669 | 1.732 | Fail |
| ASCA | Ab to Saccharomyces cervisiae (antibody to cell wall) | 0.174 | 0.294 | 1.371 | Fail |
| Autoantibody | | | | | |
| HSC 70 (HSPA8) | AutoAb to Heat Shock cognate protein 70 (constitutively expressed) | 0.151 | -0.737 | -1.451 | Succeed |
| Centromere B (CENPB) | AutoAb to centromere protein B | 0.075 | 0.214 | 1.806 | Fail |
| HSP90 alpha (HSP90AA1) | AutoAb to heat shock protein 90KD alpha | 0.091 | 0.173 | 1.712 | Fail |
| SCl 70 | AutoAb to topisomerase type 1 | 0.103 | 0.273 | 1.648 | Fail |
| Mitochondria | AutoAb to mitochondrial proteins | 0.13 | 0.107 | 1.529 | Fail |
| HSP71 (HSPA8) | AutoAb to Heat shock protein 70 (inducible) | 0.188 | 0.324 | 1.328 | Fail |

Bolded text represents statistically significant analytes associated with multivariate model and panel

FIG. 8A

TABLE 5
MALE LEFT –SIDED COLITIS
UNIVARIATE ANALYTES USED FOR MULTIVARIATE MODELING

Bolded text represents statistically significant analytes associated with multivariate model and panel

| Gene | Full Name | P value | Estimate | T value | Succeed or Fail |
|---|---|---|---|---|---|
| Protein | | | | | |
| IL7 | Interleukin 7 | 0.033 | -0.018 | -2.15 | Succeed |
| IL13 | Interleukin 13 | 0.102 | -0.016 | -1.65 | Succeed |
| CEA | Carcinoembryonic Antigen | 0.114 | -0.398 | -1.59 | Succeed |
| APOA1 | Apolipoprotein A-1 | 0.13 | -3.668 | -1.52 | Succeed |
| ACE | Angiotensin 1 converting enzyme | 0.131 | -0.009 | -1.52 | Succeed |
| THPO | Thrombopoietin | 0.137 | -0.385 | -1.5 | Succeed |
| CKM | Creatine Kinase Brain/Muscle | 0.146 | -2.407 | -1.46 | Succeed |
| LPA | Lipoprotein A | 0.17 | -0.004 | -1.37 | Succeed |
| CCL2 | Monocyte chemotactic protein 1 | 0.182 | -0.002 | -1.34 | Succeed |
| A2M | Alpha 2 macroglobulin | 0.197 | -1.19 | -1.29 | Succeed |
| MMP9 | Matrix metallopeptidase -9 | 0.075 | 0.062 | 1.8 | Fail |
| LEP | Leptin | 0.097 | 0.074 | 1.67 | Fail |
| PRL | Prolactin | 0.099 | 0.150 | 1.66 | Fail |
| GSTM1 | Glutathione S-Transferase mu 1 | 0.109 | 0.688 | 1.62 | Fail |
| IgA | Immunoglobulin A | 0.146 | 0.189 | 1.47 | Fail |
| CRP | C - reactive protein | 0.158 | 0.051 | 1.42 | Fail |
| Progesterone | | 0.161 | 0.081 | 1.41 | Fail |
| CALCA | Calcitonin | 0.182 | 0.062 | 1.34 | Fail |
| Antibody to infectious agent | | | | | |
| V Zoster | Ab to Varicella Zoster | 0.029 | 0.049 | 2.21 | Fail |
| HSV 1gD | Ab to Herpes Simplex virus type 1 glycoprotein D | 0.061 | 0.006 | 1.9 | Fail |
| HSV2gG | Ab to Herpes Simplex virus type 1 glycoprotein G | 0.069 | 0.008 | 1.84 | Fail |
| M.Tuberculosis | Ab to Mycobacterium Tuberculosis | 0.072 | 0.084 | 1.82 | Fail |
| EBNA | Ab to epstein barr virus nuclear antigen | 0.08 | 0.007 | 1.77 | Fail |
| T pallidum 15Kd | Ab to Treponema pallidum recombinant 15Kd protein | 0.095 | 0.051 | 1.68 | Fail |
| HSV ½ | Ab to Herpes Simplex virus 1/2 | 0.152 | 0.028 | 1.44 | Fail |
| Hep A | Ab to Hepatitis A | 0.154 | 0.136 | 1.44 | Fail |

FIG. 8B
TABLE 5 (continuation)
MALE LEFT –SIDED COLITIS
UNIVARIATE ANALYTES USED FOR MULTIVARIATE MODELING

| | Autoantibody | | | | |
|---|---|---|---|---|---|
| pANCA | AutoAb to myeloperoxidase | 0.012 | 0.416 | 2.56 | Fail |
| Collagen type 1 | AutoAb to collagen type 1 | 0.027 | 0.006 | 2.24 | Fail |
| Mitochondria | AutoAb to mitochondrial proteins | 0.085 | 0.235 | 1.74 | Fail |

FIG. 9

TABLE 6
FEMALE PROCTOSIGMOIDITIS
UNIVARIATE ANALYTES USED FOR MULTIVARIATE MODELING

| Gene | Full Name | P value | Estimate | T value | Succeed or Fail |
|---|---|---|---|---|---|
| Protein | | | | | |
| FABP (2or 4) | Fatty acid binding protein 2 or 4 | 0.099 | -0.223 | -1.665 | Succeed |
| C3a | ASPC3a des arg | 0.113 | -0.001 | -1.596 | Succeed |
| Testosterone | | 0.115 | -1.037 | -1.587 | Succeed |
| CD40LG | CD40 ligand | 0.164 | -0.341 | -1.401 | Succeed |
| IFNG | Interferon gamma | 0.182 | -0.289 | -1.341 | Succeed |
| CCL22 | Monocyte derive cytokine | 0.010 | 0.003 | 2.622 | Fail |
| CGA/TSHb | thyroid stimulating hormone alpha/beta | 0.046 | 0.480 | 2.022 | Fail |
| FGF2 | Fibroblast growth factor 2 | 0.072 | 0.006 | 1.817 | Fail |
| IL2 | Interleukin 2 | 0.127 | 0.148 | 1.537 | Fail |
| IL25 | Interleukin 25 | 0.132 | 0.038 | 1.517 | Fail |
| VWF | Von Willebrands factor | 0.179 | 0.019 | 1.352 | Fail |
| Antibody to infectious agent | | | | | |
| Cholera Toxin | Ab to Cholera Toxin | 0.020 | -1.145 | -2.352 | Succeed |
| L.donovani | Ab to Leishmania donovani | 0.024 | -1.228 | -2.282 | Succeed |
| Strept O SLO | Ab to Streptococcal Streptolysin oxygen labile exotoxin | 0.054 | -0.055 | -1.942 | Succeed |
| CMV | Ab to Cytomegalovirus | 0.065 | -0.092 | -1.863 | Succeed |
| Hep B core | Ab to Hepatitis B core protein | 0.086 | -0.381 | -1.731 | Succeed |
| H. pylori | Ab to H. pylori | 0.109 | -0.022 | -1.617 | Succeed |
| Hep A | Ab to Hepatitis A | 0.135 | -0.255 | -1.505 | Succeed |
| Hep B Env | Ab to Hepatitis B envelope protein | 0.144 | -0.212 | -1.472 | Succeed |
| Tetanus Toxoid | Ab to tetanus toxoid | 0.023 | 0.009 | 2.297 | Fail |
| EBNA | Ab to epstein barr virus nuclear antigen | 0.091 | 0.011 | 1.178 | Fail |
| Lyme | Ab to lyme disease | 0.094 | -0.049 | -1.688 | Fail |
| Influenza A H3N2 | Ab to Influenza A H3N2 | 0.101 | 0.003 | 1.562 | Fail |
| Hep C NS3 | Ab to Hepatitis C non-structural protein 3 | 0.120 | 0.302 | 1.568 | Fail |
| HTLCV1/2 | Ab to Human T cell lymphotrophic virus 1/2 | 0.175 | 0.037 | 1.364 | Fail |
| Autoantibody | | | | | |
| Histone H4 | AutoAb to Histone H4 | 0.102 | -0.687 | -1.646 | Succeed |
| GAD | AutoAb to Pancreatic islet cell glutamate decarboxylase | 0.174 | -0.801 | -1.368 | Succeed |
| Mitochondria | AutoAb to mitochondrial proteins | 0.128 | 0.000 | 1.531 | Fail |
| Thyroglobuilin | AutoAb to Thyroglobulin | 0.175 | 0.029 | 1.366 | Fail |
| T3 | AutoAb to triiodothyronine | 0.179 | 0.207 | 1.351 | Fail |

FIG. 10

TABLE 7
MALE PROCTOSIGMOIDITIS
UNIVARIATE ANALYTES USED FOR MULTIVARIATE MODELING

| Gene | Full Name | P value | Estimate | T value | Succeed or Fail |
|---|---|---|---|---|---|
| Protein | | | | | |
| CD40LG | CD40 ligand | 0.007 | -0.559 | -2.739 | Succeed |
| EGF | Epidermal growth factor | 0.009 | -0.005 | -2.655 | Succeed |
| THPO | Thrombopoietin | 0.043 | -0.455 | -2.037 | Succeed |
| IgE | Immunoglobulin E | 0.131 | -0.016 | -1.517 | Succeed |
| KLK3 | Prostate Specific Antigen (PSA), Free | 0.172 | -1.750 | -1.369 | Succeed |
| IL25 | Interleukin 25 | 0.199 | -0.102 | -1.291 | Succeed |
| A2M | Alpha 2 macroglobulin | 0.047 | 1.515 | 2.000 | Fail |
| ILRN | Interleukin 1 Receptor Antagonist | 0.062 | 0.002 | 1.878 | Fail |
| CALCA | Calcitonin | 0.153 | 0.077 | 1.435 | Fail |
| IL2 | Interleukin 2 | 0.155 | 0.164 | 1.426 | Fail |
| CXCL8 | Interleukin 8 | 0.158 | 0.007 | 1.417 | Fail |
| GCG | Glucagon | 0.177 | 0.030 | 1.357 | Fail |
| PRL | Prolactin | 0.188 | 0.048 | 1.322 | Fail |
| CGA/THS | Thyroid stimulating hormone | 0.584 | 0.228 | 1.907 | Fail |
| Antibody to infectious agent | | | | | |
| Hep A | Ab to Hepatitis A | 0.071 | -0.220 | -1.814 | Succeed |
| M Tuberculosis | Ab to Mycobacterium Tuberculosis | 0.141 | -0.087 | -1.479 | Succeed |
| H. Pylori | Ab to H. pylori | 0.198 | -0.006 | -1.292 | Succeed |
| L donovani | Ab to Leishmania donovani | 0.049 | 0.578 | 1.981 | Fail |
| T. Cruzi | Ab to Trypanosoma Cruzi | 0.064 | 0.324 | 1.869 | Fail |
| Hep C NS5 | Ab to Hepatitis C non-structural protein 5 | 0.126 | 0.462 | 1.539 | Fail |
| HIV1 p24 | Ab to HIV 1 p24 (gag or capsid p24) | 0.171 | 0.294 | 1.374 | Fail |
| Autoantibody | | | | | |
| HSC70 | AutoAb to Heat Shock cognate protein 70 (constitutively expressed) | 0.064 | -0.694 | -1.869 | Succeed |
| C1q | AutoAb to complement protein C1q | 0.098 | -0.019 | -1.663 | Succeed |
| cANCA | AutoAb to proteinase 3 | 0.052 | 0.062 | 1.955 | Fail |
| Insulin | AutoAb to Insulin | 0.067 | 0.424 | 1.844 | Fail |
| Thyroglobulin | AutoAb to Thyroglobulin | 0.069 | 0.036 | 1.834 | Fail |
| T3 | AutoAb to triiodothyronine | 0.136 | 0.185 | 1.498 | Fail |

Bolded text represents statistically significant analytes associated with multivariate model and panel

FIG. 11

Table 8
MALE

| Gene | Protein | Indication of Location (bolded - odds ratio greater than 1.3 or less than .775) |
|---|---|---|
| SERPINA1 | Alpha-1 antitrypsin | Proct M < LS M < Ext/Pan M |
| CD40L | CD40 ligand | Proct M < LS M < Ext/Pan M |
| FGF2 | Fibroblast growth factor 2 | Proct M < LS M < Ext/Pan M |
| CCL22 | Macrophage derived chemokine | Proct M ≤ LS M < Ext/Pan M |
| RETN | Resistin | Proct M < LS M < Ext/Pan M |
| TNFRSF1B | Tumor necrosis factor receptor superfamily member 1B | Proct M < LS M < Ext/Pan M |
| CALCA | Calcitonin | Proct M < LS M < Ext/Pan M |
| MUC16 Or CA19.9 | Ca 125 Ca19.9 | Proct M < LS M < Ext/Pan M |
| ICAM1 | ICAM-1 | Proct M < LS M < Ext/Pan M |
| SERPINE1 | Plasminogen Activator Inhibitor 1 | Proct M < LS M < Ext/Pan M |
| cANCA | AutoAb to proteinase 3 (cytoplasmic) | Proct M < LS M < Ext/Pan M |
| CCL11 | Eotaxin-1 | Proct M < Ext/Pan M < LS M |
|  | Antibodies to T. Cruzi | LS M < Proct M < Ext/Pan M |

Bolded text represents statistically significant analytes associated with multivariate model and panel

FIG. 12

TABLE 9
MALE LOCATIONS

Proctosigmoiditis Male

| Gene | Protein | Indication of Location | | |
|------|---------|------------------------|---|---|
| SERPINA1 | Alpha-1 antitrypsin | Proct M<LS M | p= .036 | OR 1.6 |
| | | Proct M <Ext/Pan M | p= .004 | OR 2.19 |
| CALCA | Calcitonin | Proct M<LS M | p= .040 | OR 1.064 |
| | | Proct M <Ext/Pan M | p= .036 | OR 1.082 |
| MUC16 Or CA19.9 | Ca 125 Ca19.9 | Proct M<LS M | p= .0006 | OR 1.034 |
| | | Proct M <Ext/Pan M | p= .0004 | OR 1.037 |
| CCL11 | Eotaxin-1 | Proct M<LS M | p= .0003 | OR 1.003 |
| | | Proct M <Ext/Pan M | p= .034 | OR 1.002 |
| ICAM1 | ICAM-1 | Proct M<LS M | p= .016 | OR 1.008 |
| | | Proct M <Ext/Pan M | p= .0069 | OR 1.011 |
| SERPINE1 | Plasminogen Activator Inhibitor 1 | Proct M<LS M | p= .039 | OR 1.002 |
| | | Proct M <Ext/Pan M | p= .005 | OR 1.005 |
| | cANCA Autoantibodies to proteinase 3 (cytoplasmic) | Proct M<LS M | p= .040 | OR 1.042 |
| | | Proct M <Ext/Pan M | p= .037 | OR 1.046 |

Left-Sided Male

| Gene | Protein | Indication of Location | | |
|------|---------|------------------------|---|---|
| TNFRSF1B | Tumor necrosis factor receptor superfamily member 1B | LS M>Proct M | p=.014 | OR .814 |
| | | LS M<Ext/Pan M | p= .021 | OR 1.247 |

Extensive/Pancolits Male

| Gene | Protein | Indication of Location | | |
|------|---------|------------------------|---|---|
| CD40L | CD40 ligand | Ext/Pan M >LS M | p= .023 | OR .774 |
| | | Ext/Pan M > Proct M | p= .012 | OR .765 |
| FGF2 | Fibroblast growth factor 2 | Ext/Pan M >LS M | p= .044 | OR .995 |
| | | Ext/Pan M >Proct M | p= .0009 | OR .993 |
| CCL22 | Macrophage derived chemokine | Ext/Pan M >LS M | p= .025 | OR .998 |
| | | Ext/Pan M > Proct M | p= .022 | OR .998 |
| RETN | Resistin | Ext/Pan M >LS M | p= .0009 | OR .819 |
| | | Ext/Pan M > Proct M | p= .00001 | OR .728 |
| | Antibodies to T. Cruzi | Ext/Pan M >LS F | p= .019 | OR .722 |
| | | Ext/Pan M > Proct M | p= .022 | OR .743 |
| TNFRSF1B | Tumor necrosis factor receptor superfamily member 1B | Ext/Pan M >LS F | p= .021 | OR .801 |
| | | Ext/Pan M > Proct F | p= .00003 | OR .652 |

FIG. 13

TABLE 10 MALE

| GENE or Antibody | PROTOSIGMOIDITIS | | | LEFT-SIDED | | | PAN/EXTENSIVE | | |
|---|---|---|---|---|---|---|---|---|---|
| | average | median | range | average | median | range | average | median | range |
| SERPINA1 (mg/ml) | 1.75 | 1.70 | .90-4 | 1.90 | 1.80 | .99-3.7 | 2.03 | 1.85 | 1-4.2 |
| MUC 16 (U/ml) | 11.91 | 10.50 | 4.35-50.10 | 15.13 | 14.80 | 4.35-36.4 | 19.79 | 11.35 | 4.35-316 |
| CA19.9 (U/ml) | 7.14 | 5.00 | .78-38.60 | 10.95 | 6.15 | .78-106 | 8.98 | 5.35 | .8-56.4 |
| CALCA (pg/ml) | 8.11 | 6.50 | 1.60-20.50 | 9.24 | 8.30 | 1.6-32.9 | 9.62 | 8.30 | 1.6-24.5 |
| CD40L (ng/ml) | 1.66 | 1.40 | .01-7.2 | 1.68 | 1.35 | .04-9 | 2.31 | 2.10 | .0065-7 |
| CCL11 (pg/ml) | 238.61 | 210.00 | 9.50-736 | 333.51 | 268.50 | 55.10-1840 | 291.39 | 268.00 | 9.5-1100 |
| CCL22 (pg/ml) | 560.84 | 532.00 | 185-1580 | 556.95 | 538.50 | 236-1160 | 656.37 | 612.50 | 49.9-2080 |
| SERPINE1 (ng/ml) | 240.06 | 234.00 | 36.9-458 | 265.53 | 256.00 | 64.60-621 | 287.61 | 276.00 | 117-821 |
| RETN (ng/ml) | 3.52 | 3.20 | .93-12.70 | 3.90 | 3.55 | .96-11.80 | 4.99 | 4.15 | 1.4-13.6 |
| TNFRSF1B (ng/ml) | 4.32 | 4.20 | 1.60-9.10 | 4.82 | 4.60 | 2-10.10 | 5.60 | 4.95 | 2.5-12.6 |
| Antibodies to T. Cruzi (MFI) | 4.15 | 4.00 | 2-10.4 | 4.12 | 3.80 | 1.6-9.7 | 4.65 | 4.40 | 2.1-8.5 |
| cANCA (MFI) | 6.00 | 4.60 | 1.60-42.25 | 8.44 | 5.00 | 2-100.33 | 9.07 | 5.30 | 2.6-42.7 |
| FGF2 | 121.20 | 107.00 | 52-329 | 135.15 | 105.00 | 52-329 | 339.50 | 322.2 | 248-578 |

FIG. 14

Table 11
FEMALE

| Gene/Antigen | Protein | Indication of Location (bolded - odds ratio greater than 1.3) |
|---|---|---|
| SERPINA1 | Alpha-1 antitrypsin | Proct F < LS F < Ext/Pan F |
| B2M | Beta 2 microglobulin | Proct F < LS F < Ext/Pan F |
| C3 | ASP (C3a des Arg) | Proct F < LS F ≤ Ext/Pan F |
| MMP3 | Matrix metallopeptidase 3 | Proct F < LS F < Ext/Pan F |
| RETN | Resistin | Proct F < LS F < Ext/Pan F |
| IL6 | Interleukin 6 | Proct F < LS F < Ext/Pan F |
| TNFRSF1B | Tumor necrosis factor receptor superfamily member 1B | Proct F < LS F < Ext/Pan F |
|  | Antibodies to CMV | Proct F < LS F < Ext/Pan F |
|  | Antibodies to Lyme | Proct F < LS F < Ext/Pan F |
| F7 | Coagulation Factor VII | Proct F ≤ Ext/Pan F < LS F |
| SERPINA7 | Thyroxin binding globulin | Proct F < Ext/Pan F < LS F |
| IFNG | Gamma Interferon | LS F < Proct F < Ext/Pan F |
|  | Auto antibody to RNPa | LS F < Proct F < Ext/Pan F |
|  | Auto antibody to RNP | LS F < Proct F < Ext/Pan F |
| GSTM1 | Glutathione S-Transferase Mu-1 | LS F < Ext/Pan F < Proct F |
| BDNF | Brain derived neurotrophic factor | Ext/Pan F < LS F < Proct F |
| THPO | Thrombopoietin | Ext/Pan F < LS F ≤ Proct F |

FIG. 15

TABLE 12
FEMALE LOCATIONS

Proctosigmoiditis Female

| Gene | Protein | Indication of Location | | |
|---|---|---|---|---|
| SERPINA1 | Alpha-1 antitrypsin | Proct F<LS F | p= .002 | OR 2.3 |
| | | Proct F <Ext/Pan F | p= .0004 | OR 3.31 |
| C3 | ASP (C3a des Arg) | Proct F<LS F | p= .037 | OR 1.0005 |
| | | Proct F <Ext/Pan F | p=.041 | OR 1.0007 |
| B2M | Beta 2 microglobulin | Proct F<LS F | p= .021 | OR 2.058 |
| | | Proct F <Ext/Pan F | p= .008 | OR 2.826 |
| F7 | Coagulation Factor VII | Proct F<LS F | p= .0008 | OR 1.003 |
| | | Proct F <Ext/Pan F | p= .048 | OR 1.002 |
| MMP3 | Matrix metallopeptidase 3 | Proct F<LS F | p= .028 | OR 1.092 |
| | | Proct F <Ext/Pan F | p= .016 | OR 1.124 |
| RETN | Resistin | Proct F<LS F | p= .004 | OR 1.386 |
| | | Proct F <Ext/Pan F | p= .002 | OR 1.546 |
| SERPINA7 | Thyroxin binding globulin | Proct F<LS F | p= .002 | OR 1.024 |
| | | Proct F <Ext/Pan F | p= .018 | OR 1.024 |
| TNFRSF1B | Tumor necrosis factor receptor superfamily member 1B | Proct F<LS F | p= .023 | OR 1.243 |
| | | Proct F<Ext/Pan F | p= .022 | OR 1.326 |

Left Sided Female

| Gene | Protein | Indication of Location | | |
|---|---|---|---|---|
| GSTM1 | Glutathione S-Transferase Mu-1 | LS F< Proct F | p=. 031 | OR 1.656 |
| | | LS F< Ext/Pan F | p= .073 | OR 1.91 |
| IFNG | Gamma Interferon | LS F< Proct F | p= .109 | OR 1.18 |
| | | LS F< Ext/Pan F | p= .016 | OR 1.34 |

Extensive/Pancolits Female

| Gene | Protein | Indication of Location | | |
|---|---|---|---|---|
| BDNF | Brain derived neurotrophic factor | Ext/Pan F <LS F | p= .004 | OR 1.08 |
| | | Ext/Pan F < Proct F | p= .008 | OR 1.07 |
| THPO | Thrombopoietin | Ext/Pan F <LS F | p= .005 | OR 1.88 |
| | | Ext/Pan F < Proct F | p= .004 | OR 1.87 |
| | Antibodies to CMV | Ext/Pan F >LS F | p= .057 | OR .942 |
| | | Ext/Pan F > Proct F | p= .036 | OR .940 |
| | Antibodies to Lyme | Ext/Pan F >LS F | p= .058 | OR .964 |
| | | Ext/Pan F > Proct F | p= .027 | OR .960 |
| | Auto antibody to RNPa | Ext/Pan F >LS F | p= .039 | OR .922 |
| | | Ext/Pan F > Proct F | p= .091 | OR .964 |
| | Auto antibody to RNP | Ext/Pan F >LS F | p= .037 | OR .922 |
| | | Ext/Pan F > Proct F | p= .089 | OR .976 |
| IL6 | Il 6 | Ext/Pan F >LS F | p= .074 | OR .930 |
| | | Ext/Pan F > Proct F | p= .047 | OR .927 |

FIG. 16

FEMALE- TABLE 13

| GENE or Antibody | PROTOSIGMOIDITIS | | | LEFT-SIDED | | | PAN/EXTENSIVE | | |
|---|---|---|---|---|---|---|---|---|---|
| | mean | median | range | mean | median | range | mean | median | range |
| SERPINA1 (mg/ml) | 1.65 | 1.60 | 0.92-3.10 | 1.92 | 1.75 | 0.75-4.40 | 2.11 | 1.95 | 0.78-3.80 |
| C3 (ASP C3a des Arg) (ng/ml) | 2733 | 2685 | 1710-4380 | 2913 | 2795 | 1980-6530 | 2968 | 2915 | 1890-4350 |
| B2M (µg/ml) | 1.38 | 1.30 | 0.5-4.00 | 1.55 | 1.50 | 0.67-2.90 | 1.66 | 1.60 | 0.54-2.80 |
| BDNF (ng/ml) | 19.09 | 18.15 | 2.4-41.00 | 19.73 | 19.00 | 0.96-44.90 | 14.26 | 13.40 | 1.3-33.60 |
| F7 (ng/ml) | 429.53 | 411 | 110-861 | 518.09 | 495.50 | 135-1490 | 490.57 | 496 | 199-685 |
| IL6 (pg/ml) | 2.78 | 0.92 | 0.82-30.80 | 2.81 | 1.85 | 0.82-22.70 | 4.84 | 1.70 | 0.78-22.80 |
| MMP3 (ng/ml) | 5.45 | 4.70 | 0.033-17.40 | 6.76 | 5.70 | 0.033-20.50 | 7.50 | 6.20 | 1.3-29.70 |
| RETN (ng/ml) | 3.32 | 3.15 | 1.5-10.60 | 3.93 | 3.90 | 2-9.30 | 4.24 | 3.85 | 1.4-9.00 |
| SERPINA7 (µg/ml) | 56.78 | 54.10 | 23-110 | 65.52 | 62.45 | 31.9-124 | 66.24 | 63.45 | 23.6-128 |
| TNFRSF1B (ng/ml) | 4.05 | 3.75 | 1.7-10.80 | 4.57 | 4.40 | 1.7-10.10 | 4.81 | 4.65 | 1.5-10.30 |
| THPO (ng/ml) | 3.53 | 3.40 | 0.85-8.20 | 3.54 | 3.40 | 1.7-7.00 | 2.86 | 3.05 | 0.58-4.10 |
| Antibodies to CMV (MFI) | 14.02 | 13.90 | 2.8-31.00 | 14.35 | 13.98 | 3.5-32.25 | 16.99 | 15.05 | 4.2-37.25 |
| Antibodies to Lyme (MFI) | 20.28 | 20.37 | 2.1-47.38 | 21.20 | 19.90 | 2.7-47.50 | 25.54 | 22.83 | 5.7-52.88 |
| Auto antibody to RNPa (MFI) | 5.77 | 4.25 | 2-44.83 | 4.79 | 3.55 | 1-29.00 | 9.23 | 4.95 | 2-74.80 |
| Auto antibody to RNP (MFI) | 33.79 | 33.54 | 3-77.88 | 32.19 | 30.81 | 2.7-86 | 39.08 | 39.15 | 14.35-73.25 |
| IFNG | 2.42 | 2.01 | ND[a]-8.16 | 2.36 | 2.09 | ND[a]-9.06 | 2.70 | 1.72 | ND[a]-12.90 |
| GSTM1 | 0.40 | 0.38 | ND[a]-0.77 | 0.36 | 0.31 | ND[a]-0.85 | 0.46 | 0.40 | ND[a]-.89 |

ND[a] = not detectable

PROCESS AND SYSTEM FOR PREDICTING RESPONDERS AND NON-RESPONDERS TO MESALAMINE TREATMENT OF ULCERATIVE COLITIS

This application is a divisional application of and claims benefit in its entirety of U.S. patent application Ser. No. 15/068,981 filed Mar. 14, 2016, titled: Process and System for Predicting Responders and Non-Responders to Mesalamine Treatment of Ulcerative Colitis.

BACKGROUND OF THE INVENTION

Ulcerative colitis (UC) is a form of inflammatory bowel disease (IBD) that appears in the large intestine or colon with periods of exacerbated symptoms and periods that are relatively symptom free. UC patients often experience the same symptoms as irritable bowel syndrome (IBS) patients, which is a much less serious condition, making a definitive diagnosis much more complicated. Similarly, patients with indeterminate colitis may have a form of colitis that is different from UC, and more similar to Crohn's colitis, another related form of intestinal IBD.

Symptoms of UC are anatomically heterogeneous in their presentation between patients. UC patients for example can present with disease in a range of extent from the recto-sigmoid only on to degrees of involvement including the entire colon. Initially, patients treated medically may be started on non-specific anti-inflammatory medications, most commonly mesalamine (5-ASA). Non-responders to a trial of medications may then be escalated in their therapy with cytotoxic or biologic medications. This "step-up" approach typically using mesalamine to treat active UC, is associated with clinical treatment failures in 60% of patients with moderate UC, compared to 80% treated with placebo. Moreover, a clinical response favoring doses of mesalamine greater than 2.5 grams per day has not been clearly shown despite clinical practice to the contrary.

Since biologics are associated with significantly increased costs compared to oral anti-inflammatory drugs, the early identification of patients who do not respond to mesalamine or conversely, who would respond to other therapies is important. The "step-up" medication strategy currently used does not take gender difference into consideration nor the locations of the disease within the colon. The same drug intervention strategy is applied to almost all UC patients, which is believed to be one of the key factors responsible for the high clinical treatment failure.

Numerous systems have been developed for inflammatory bowel disease (IBD) biomarkers including the use of fecal calprotectin and lactoferrin proteins for identifying patients with inflammatory bowel disease (IBD), assessing disease severity and for predicting relapses; the use of serum anti-*Saccharomyces cerevisiae* antibody (ASCA) and perinuclear antoneutriphil cytoplasmic antibody (pANCA) biomarkers to differentiate Crohn's Disease (CD) from UC; and the use of serum anti-OmpC IgA anti-CBir1 biomarkers with ASCA and other biomarker assays for IBD diagnosis as well as UC and CD differentiation. IBD disease biomarkers including anti-GM-CSF antibody, CD11b, TNF-a, CRP, aldo-keto reductase family 1 B10 (AKR1B10), perforin, NF-kB, CXC-chemokines, aquaporins, kinesins, adaptor protein-1 (AP-1), C5a, IL-2R, integrins, HCC-4, IL-7, MCP-1, MSP protein, IL-11, G-CSF, adrenoreceptors, ST2, E-cadhein, KC, IL-12/23p40, IL-17, chlorotyrosine, PAP/REG3, MIF, DMBT1, LCN2, IL-22, haptoglobin, CCL20, IL-6, IL-33, CAP37, E4A (UBE4A), CXCL16, resistin, apolipoprotein A-IV, beta-defensin, NOD2/CARD15, NOD1/CARD4, toll-like receptors (TLR) 2 and 4, leptin, adiponectin, IL-10, DPP-IV, and CXCR4 have also been identified. Such biomarkers have been used for determining the responsiveness of steroid and biological treatments. However, until now, there have been no method or system developed for determining the responsiveness of a patient to mesalamine for the treatment of active UC.

As previously stated, one of the first lines of conventional UC clinical treatment is the use of mesalamine (5-ASA). However, the efficacy of mesalamine in active UC is only about 30-40%. UC pathophysiology and factors that influence the response to mesalamine treatment are not well known. The identified significant differences in protein profiling from different genders and anatomic colitis locations demonstrate that UC is a complicated disease. Accordingly, a need exists for a process and system for predicting the potential efficacy of a patient's response to mesalamine suffering from UC. It is also desirable to have a process and a system for developing an effective strategy for treatment of patients suffering from UC and a new, safe, effective, and potentially gender and colitis location dependent therapeutics.

SUMMARY OF THE INVENTION

The process and system of the subject invention is directed to a more effective, individual based treatment regimen which is built using clinical identified target biomarkers. In a preferred embodiment of the invention, the biomarkers identified herein establishes a foundation of UC target biomarkers associated with gender differential responses to mesalamine, and includes panels identifying protein target biomarkers that distinguishes mesalamine response differences between genders. Accordingly, the subject invention is directed to a process and system for determining the efficacy of mesalamine for patients being treated for various UC conditions. The subject invention is also directed to a process and system for developing effective strategies for the treatment of patients suffering from UC and to new, safe, effective, and potentially gender and colitis location dependent therapeutics.

Preferred embodiments of the subject invention are a process and a system that utilizes gender and disease locations to effectively develop new diagnostics and diagnostics standards for UC therapeutic strategies.

Another preferred embodiment of the subject invention utilizes gender and disease locations to permit personalized clinical UC medication regimens based on an individual patient's biomarker profiles.

Another preferred embodiment of the subject invention operates to identify mesalamine non-responders at a relatively early stage of UC using one or more panels of target biomarkers which allows for the development of a clinical medication approach having greater mesalamine efficacy.

Another preferred embodiment of the subject invention operates to identify mesalamine non-responders at a relatively early stage of UC using one or more panels of target biomarkers which allow faster and effective disease control with alternative treatments.

A preferred embodiment of the invention the panel is for male and female pancolitis and extensive colitis and comprises one or more target biomarkers selected from a list consisting of GSTM1, IL13, RETN and Histone H2a autoantibody.

Another preferred embodiment of the invention the panel is for female left sided colitis and comprises one or more target biomarkers selected from a list consisting of antibody to *L. donovani*, antibody to HTCLV1/2, and HSP90alpha autoantibody.

Another preferred embodiment of the invention the panel is for male left sided colitis and comprises one or more target biomarkers selected from a list consisting of APOA1, PRL, HSP 71 autoantibody and IgA.

Another preferred embodiment of the invention the panel is for female proctosigmoiditis and comprises one or more target biomarkers selected from the list consisting of CCL22 and antibody to cholera toxin.

Another preferred embodiment of the invention the panel is for male proctosigmoiditis and comprises one or more target biomarkers selected from the list consisting of ILRN and CD40 LG.

A preferred embodiment of the invention, the identified target biomarkers are gender dependent biomarkers.

Another preferred embodiment of the invention the identified target biomarkers are effective for predicting efficacy of mesalamine patients with pancolitis and extensive colitis.

Another preferred embodiment of the invention the identified target biomarkers are effective for predicting efficacy of mesalamine 2.4 g and 4.8 g daily therapy, given for 6 weeks to female and male patients with pancolitis and extensive colitis, and are selected from a panel comprising a list having one or more target biomarkers consisting of Model 1: GSTM1, IL13 and Histone H2a autoantibody and Model 2: Histone H2A autoantibody and REIN target biomarkers.

Another preferred embodiment of the invention the identified target biomarkers are effective for predicting the efficacy of mesalamine 2.4 g and 4.8 g daily therapy, given for 6 weeks for female patients with left-sided colitis, and are selected from a panel comprising a list one or more target biomarkers consisting of antibody to *L. donovani*, antibody to HTCLV 1/2, HSP90 alpha autoantibody target biomarkers.

Another preferred embodiment of the invention the identified target biomarkers are effective for predicting the efficacy of mesalamine 2.4 g and 4.8 g daily therapy, given for 6 weeks for male patients with left-sided colitis, and are selected from the panel comprising a list of one or more target biomarkers consisting of HSP 71 autoantibody, IgA, APOA1 and PRL target biomarkers.

Another preferred embodiment of the invention the identified target biomarkers are effective for predicting the efficacy of mesalamine 2.4 g and 4.8 g daily therapy, given for 6 weeks for female patients with proctosigmoiditis and are selected from the panel comprising a list of one or more target biomarkers consisting of CCL22, and antibody to cholera toxin.

Another preferred embodiment of the invention the identified target biomarkers are effective for predicting the efficacy of mesalamine 2.4 g and 4.8 g daily therapy, given for 6 weeks for male patients with proctosigmoiditis, and are selected from a panel comprising a list of one or more target biomarkers consisting of IL1RN, and CD40L.

A preferred embodiment of the invention is a process for predicting a patient's response to mesalamine for the treatment of ulcerative colitis (UC), the process comprises the steps of: identifying a patient diagnosed with UC; determining the location of the ulcerative colitis; obtaining a blood sample from the patient; using the sample to form a blood component; selecting a panel having one or more target biomarkers for the diagnosed UC, location and gender of the patient; using the blood component to make a determination as to the existence and quantity of one or more of the target biomarkers in the blood component; and using the determination to create an outcome that predicts the effectiveness of mesalamine treatment for the patient.

In a preferred embodiment of the invention the panel comprises levels of one or more target biomarkers selected from the list consisting of GSTM1, IL13, RETN and Histone H2a autoantibody effective for use in creating outcomes for male and female patients having pancolitis and extensive colitis.

In a preferred embodiment of the invention the panel comprises levels of one or more target biomarkers selected from the list consisting of antibody to *L. donovani*, antibody to HTCLV 1/2 and HSP90alpha autoantibody effective for use in creating outcomes for female left sided colitis.

In a preferred embodiment of the invention the panel comprises levels of one or more target biomarkers selected from the list consisting of APOA1, PRL, HSP 71 autoantibody and IgA effective for use in creating outcomes for male left sided colitis.

In a preferred embodiment of the invention the panel comprises one or more target biomarkers selected from the list consisting of CCL22 and antibody to cholera toxin effective for use in creating outcomes for female proctosigmoiditis.

In a preferred embodiment of the invention the panel comprises one or more target biomarkers selected from the list consisting of ILRN and CD40 LG effective for use in creating outcomes for male proctosigmoiditis.

In a preferred embodiment of the invention one or more panels are effective for predicting efficacy of mesalamine patients with pancolitis and extensive colitis.

Another preferred embodiment of the invention is a process for defining specific UC disease biomarkers as to gender and colitis locations comprising the steps of: obtaining a sample from the patient; using the sample to form a blood component, such as a serum, identifying one or more target biomarkers from the blood component and the levels of the identified target biomarkers, and using the levels of the identified target biomarkers to create an outcome that diagnoses mild-to-moderate ulcerative colitis disease.

In a preferred embodiment of the invention the process further comprises the step of using the panel and the levels and/or the change in levels of the one or more target biomarkers to develop novel UC therapeutics as new drug targets or as means to identify new drug targets or as means to screen new drug therapeutics.

A preferred embodiment of the invention is a process for predicting a patient's response to mesalamine for the treatment of ulcerative colitis (UC), the process comprises the steps of identifying a patient diagnosed with UC, determining the location of the UC, obtaining a first blood sample from the patient, mixing the blood sample with one or more separators to create a first blood component, selecting a panel, wherein the panel identifies one or more target biomarkers for the location of the UC and the gender of the patient, determining the level of each of the one or more target biomarkers in the first blood component, making a first comparison of the levels of the one or more target biomarkers in the first blood component to levels in a reference, and using the first comparison to create an outcome predicting the effectiveness of mesalamine treatment for the patient.

A preferred embodiment of the invention is a process for the treatment of ulcerative colitis (UC), the process comprises the steps of identifying a patient diagnosed with UC, determining the location of the UC, obtaining a first blood sample from the patient, creating a blood component devoid of red and white blood cells by mixing the first blood sample with one or more separators, selecting a panel based on the location and gender of the UC wherein the panel identifies one or more target biomarkers, making a determination of the existence and level of the one or more of the identified target biomarkers in the first blood component, administering a treatment to the patient for the UC, obtaining a second blood sample from the patient and mixing the second blood sample with one or more separators to create a second blood component, determining the level of each of the one or more target biomarkers in the second blood component, making a second comparison of the levels of the one of more target biomarkers in the second blood component to the levels of the one or more target biomarkers in the first blood component, and using the second comparison to evaluate the effectiveness of the treatment.

In a preferred embodiment of the invention the process further comprising the steps of identifying one or more compounds or proteins that effect, produces, or modifies one or more of the identified target biomarkers, and creating a treatment for the UC disease wherein such treatment is based on one or more of the identified compounds or proteins.

In another preferred embodiment of the invention further comprising the steps of identifying changes in one or more of the target biomarkers caused by one or more compounds or proteins and using the identified changes to analyze the disease mechanism of the type of UC being evaluated.

A preferred embodiment of the invention is a process for predicting a patient's response to mesalamine for the treatment of ulcerative colitis (UC), the process comprises the steps of: identifying the location of the UC, obtaining a blood sample from the patient diagnosed with the UC, forming a blood component by mixing the blood sample with one or more separators, selecting a panel identifying one or more target biomarkers based on the location and gender of the patient, using the blood component to make a determination as to the existence and quantity of one or more of said target biomarkers in the blood component, and using the determination to create an outcome that predicts the effectiveness of mesalamine treatment for the patient.

In a preferred embodiment of the invention the one or more separators are selected from the list consisting of an EDTA coated tube, and/or a Heparin coated tube, and/or a Citrate coated tube.

In a preferred embodiment of the invention the one or more separators are anticoagulants.

Other embodiments, advantages and objects of the invention will be apparent from the following description and the appended claims.

BRIEF DESCRIPTION OF THE DRAWINGS

To provide a more complete understanding of the present invention and further features and advantages thereof, reference is now made to the following description taken in conjunction with the accompanying drawings, in which:

FIG. 3 illustrates specific biomarker panels for a patient diagnosed with UC based on the gender of the patient and the location of the UC;

FIGS. 4A and 4B shows Table 1 displaying significant univariate analytes with a p value of less than 0.2 which were used to build the final biomarker multivariate model for success or failure of male/female pan/extensive colitis and also shows distribution of proteins that predict success or failure of 5ASA within subgroups;

FIG. 5 shows Table 2 displaying descriptive ranges of location and gender specific biomarkers;

FIG. 6 shows Table 3 displaying predictive models for location and gender;

FIG. 7 shows Table 4 displaying significant univariate analytes with p values of less than 0.2 which were used to build the final biomarker multivariate model for success or failure of female left-sided colitis UC patients;

FIG. 8A and FIG. 8B shows Table 5 displaying significant univariate analytes with p vales of less than 0.2, which were used to build the final biomarker multivariate model for success or failure of male left-sided ulcerative colitis patients;

FIG. 9 shows Table 6 displaying significant univariate analytes with p value of less than 0.2, which are used to build the final biomarker multivariate model for success or failure of proctosigmoiditis UC female patients;

FIG. 10 shows Table 7 displaying male proctosigmoiditis univariate analytes used for multivariate modeling;

FIG. 11 shows Table 8 displaying a list of target biomarkers for male locations of proctosigmoiditis, left-sided colitis and extensive/pancolitis that can be used for drug development, compound screening, diagnostics, and monitoring therapeutic responses;

FIG. 12 shows Table 9 displaying a list of target biomarkers for male locations of proctosigmoiditis, left-sides and extensive/pancolitis that can be used for drug development, compound screening, diagnostics, and monitoring therapeutic responses;

FIG. 13 shows Table 10 displaying the list of target biomarkers for male proctosigmoiditis, left-sided and pan/extensive that can be used for drug development, compound screening, diagnostics, and monitoring therapeutic responses;

FIG. 14 shows Table 11 displaying a list of target biomarkers for female locations of proctosigmoiditis, left-sided and extensive/pancolitis that can be used for drug development, compound screening, diagnostics, and monitoring therapeutic responses;

FIG. 15 shows Table 12 displaying a list of target biomarkers for female locations of proctosigmoiditis, left-sides and extensive/pancolits that can be used for drug development, compound screening, diagnostics, and monitoring therapeutic responses;

FIG. 16 shows Table 13 displaying the list of target biomarkers for female proctosigmoiditis, left-sided and pan/extensive that can be used for drug development, compound screening, diagnostics, and monitoring therapeutic responses;

DETAILED DESCRIPTION OF THE INVENTION

Figure 1:
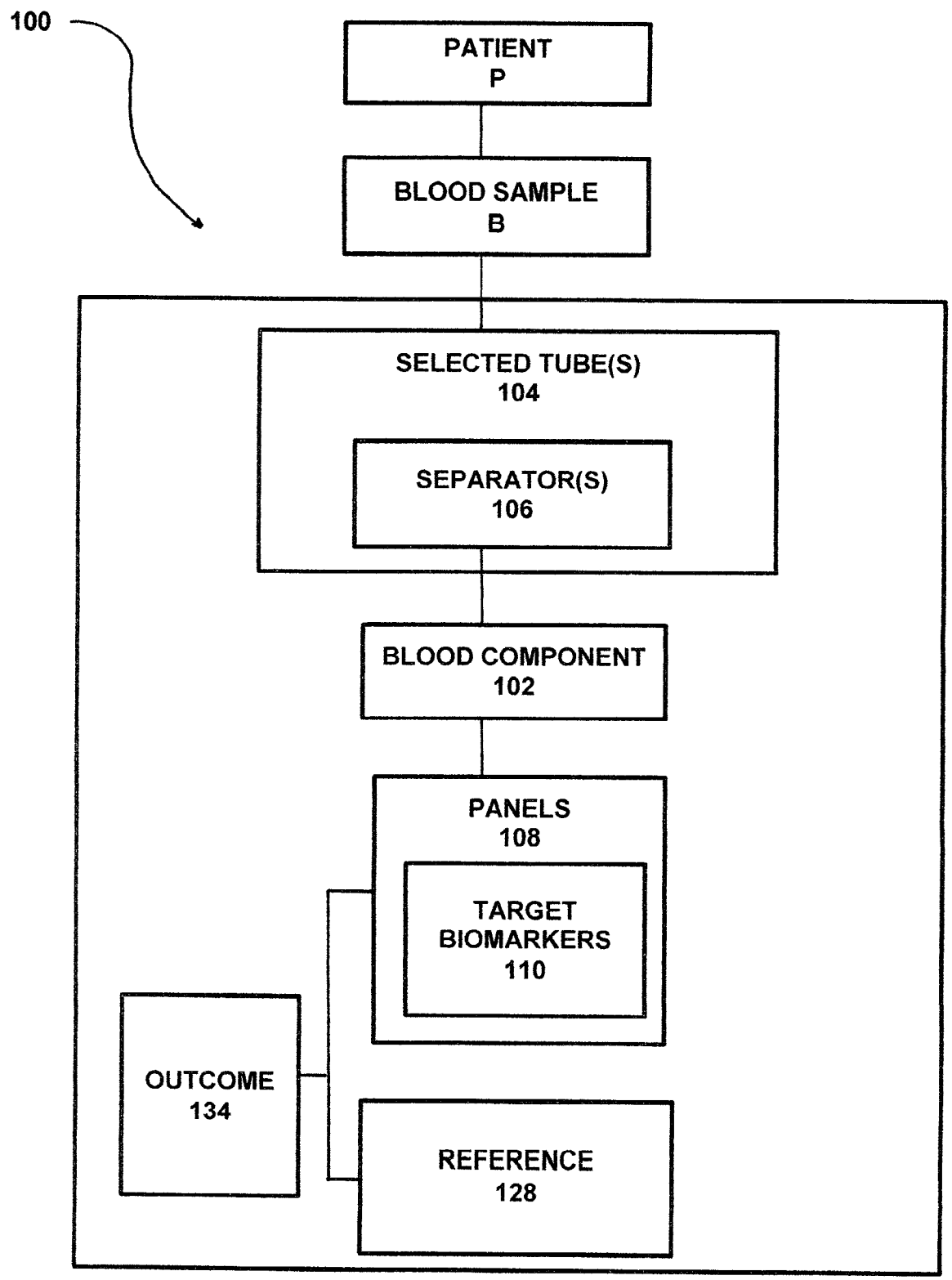
FIG. 1 is a schematic representation illustrating the system of the subject invention whereby a blood component comprising a blood sample from a patient diagnosed with a form of UC is mixed with one or more separators to form a blood component that is devoid of red and white blood cells, a panel identifying one or more target biomarkers based on gender and location of the UC, the blood component further comprises levels (quantity) of one or more target biomarkers, and a reference for comparing the levels of the target biomarkers for creating an outcome.

Using mesalamine to treat active UC is associated with clinical treatment failures in 60% of patients with moderate UC, compared to 80% of those treated with placebo. Due to the lack of understanding of disease pathophysiology, until now, mesalamine treatment did not take gender difference into consideration nor the locations of the disease within the colon. Patients, such as those with left-sided colitis and proctosigmoiditis are difficult to manage clinically. However, patients with proctosigmoiditis do not have greatly increased predilection to developing colon cancer. This is different from those patients with pancolitis and extensive colitis that have significantly higher risk of developing colon cancer. Therefore, it is desirable to have a process and system that are effective for use in specifically predicting mesalamine treatment responses for subgroups of patients having UC as well as for use in developing effective strategies for the treatment of patients suffering from UC as well as for developing new and effective therapeutics effective for the treatment of UC at different anatomic colon locations.

In a preferred embodiment, the subject invention comprises panels of protein biomarkers ("target biomarkers") that distinguish mesalamine response differences between genders and anatomic colitis locations. Using these panels of target biomarkers as described herein, mesalamine non-responders can be identified earlier. Further, using such panels of target biomarkers a new clinical medication process has been developed having greater efficacy and is faster and more effective for disease control while allowing for alternative treatments for the non-responders.

Preferably, the process or system of the subject invention comprise two categories of panels that identify target biomarkers based on their differences in utility. The first category of panels provides a list of identify target biomarkers that are gender dependent and operate to predict mesalamine treatment outcomes (success or failure) for mild-to-moderate UC patients. The method and system utilize the panels as unique tools allowing physicians to decide optimal personalized UC therapy strategies. The process and system further utilize different panels identifying target biomarkers for patients with colitis in different colonic locations.

The second category of panels provide a list of identified target biomarkers used for mild-to-moderate UC disease for specific genders at different colitis locations. The panels operate for determining and validating new UC drug targets. The panels comprise listings of identified target biomarkers that are used for new drug targets themselves, or are used in understanding UC mechanism and to determine or identify other molecules, proteins, and the like for new therapeutic targets. The panels identifying disease target biomarkers are also used as tools for screening UC therapeutic compounds, as well as for diagnosing mild-to-moderate UC.

First Category: Gender Dependent Target Biomarkers for Predicting Mesalamine Treatment Outcomes In a preferred embodiment, the system and process of the subject invention utilize a first category of gender dependent target biomarkers to create outcomes that predict the efficacy of mesalamine treatment (success or failure) on mild-to-moderate UC patients with different colitis locations (left-sided colitis, proctosigmoiditis, pancolitis, and extensive colitis).

Figure 2:
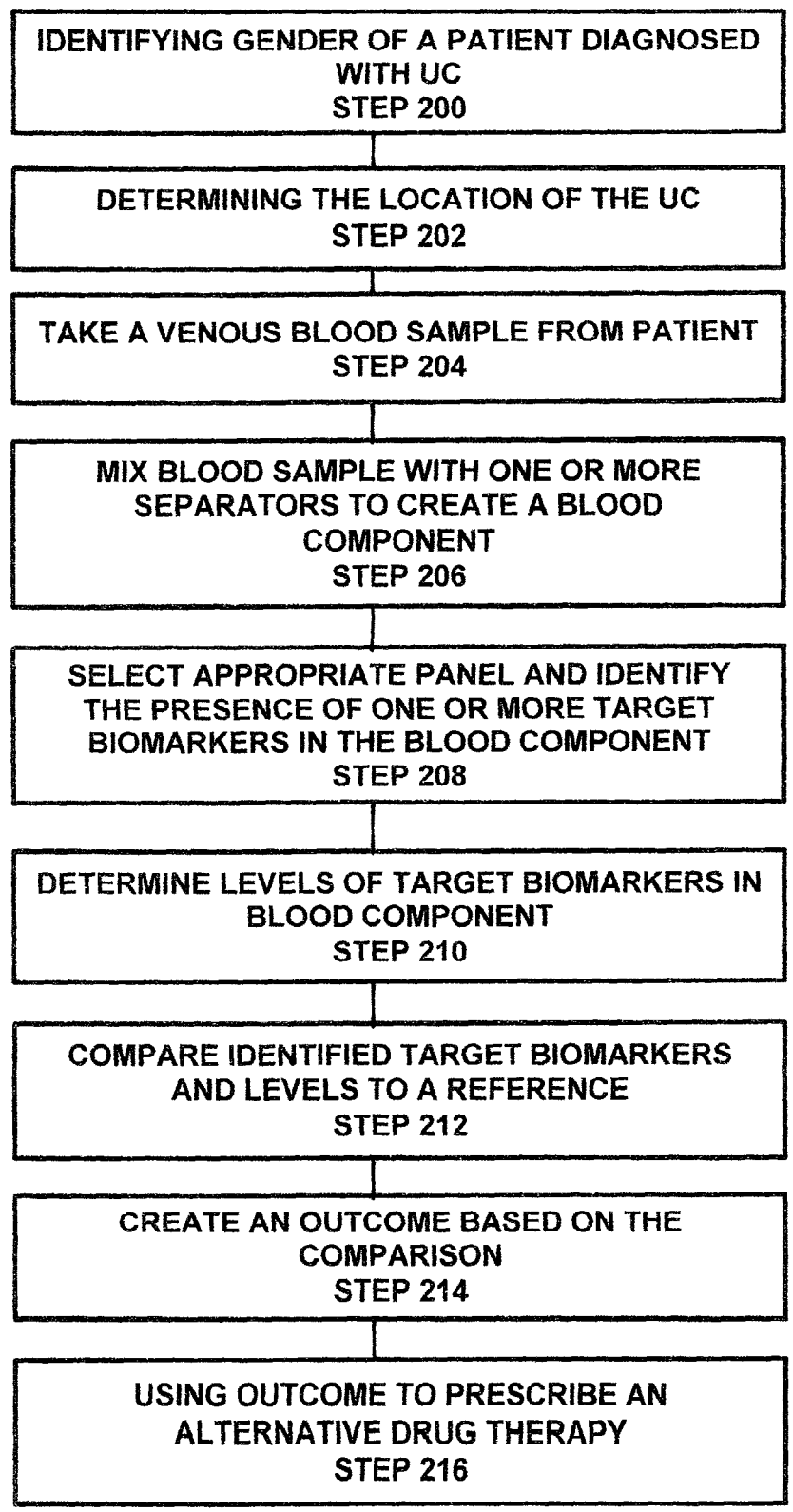
FIG. 2 is a flow diagram showing the general methodology of the process for predicting efficacy of mesalamine for patients being treated for a diagnosed UC condition.

As illustrated in FIGS. 1 and 2, the system 100 and process of the subject invention comprises identifying a patient P diagnosed with UC (step 200) and determining the location of the UC (step 202). A venous blood sample B is taken from the patient P (step 204) and a specified blood component 102, such as in the form of a serum or plasma, is created by mixing the blood sample B with one or more separators 106 (step 206). As used herein, the term "serum," unless otherwise stated, refers to both serum and plasma. In a preferred embodiment, the blood component 102 is in the form of a plasma (not a serum) and is created by placing the blood sample B into at least one selected tube 104 coated with or having one or more separators 106, such as an EDTA coated tube, and/or a Heparin coated tube, and/or a Citrate coated tube to create the specified blood component 102, such as an EDTA plasma, and/or a Heparin plasma, and/or a citrate plasma, respectively. Another preferred embodiment of the invention, the blood component 102 is in the form of a serum (not plasma) created and using a venous blood sample B drawn from a patient P into at least one selected tube 104 having one or more separators 106, such as physical serum separators (i.e. SST tubes). After the venous blood B is drawn into the selected tube 104 it is immediately inverted 3-5 times, so that the various serum separators 106 (anticoagulants), are mixed into the blood sample B creating the blood component 102 in the form of a serum (not plasma) devoid of red and white blood cells. Each of the one or more tubes 104 having the mixture of blood sample B and separators 106 is rested for up to 30-60 minutes at room temperature and then centrifuged at either room temperature or at 4-8° C. for 20 minutes at 1800-2000 rpm. For a blood component 102 in the form of a plasma, once the blood sample B is drawn into one or more of the tubes 104, the tubes are inverted 3-5 times to mix the blood sample with the separators 106 (EDTA and/or Heparin and/or Citrate) and centrifuged at either room temperature or at 4-8° C. for 20 minutes at 1800-2000 rpm. After centrifugation, the cells of the blood sample will pellet to the bottom of the tube or get separated physically by the separator and a purified blood component in the form of a serum or plasma is collected.

Referring to FIG. 3, the subject invention further utilizes one or more panels 108 identifying one or more target biomarkers 110. The one or more panels 108 preferably comprises a first panel 112 is shown and identifies gender dependent target biomarkers 110. Upon evaluation of statistical analysis data (p values, t values risk ratio, estimates and effect increments), the target biomarkers 110 identified in the first panel 112 were selected as being effective for use in predicting efficacy of mesalamine (2.4 g and 4.8 g daily therapy, given for six weeks) for female and male patients with pancolitis and extensive colitis and can be are used individually or in any combination for predicting mesalamine efficacy.

The one or more panels 108 preferably further comprises a second panel 116 identifying gender dependent target biomarkers 110 as shown and upon evaluation of statistical analysis data (p values, t values, risk ratio, estimates and effect increments), were selected as being effective for use in predicting efficacy of mesalamine (2.4 g and 4.8 g daily therapy, given for six weeks) for female patients with left-sided colitis and are used individually or in any combination for predicting mesalamine efficacy.

The one or more panels 108 preferably further comprises a third panel 120 identifying gender dependent target biomarkers 110 as shown and upon evaluation of the statistical analysis data (p values, t values, risk ratio, estimates and effect increments), were selected as being effective in predicting efficacy of mesalamine (2.4 g and 4.8 g daily therapy, given for six weeks) for male patients with left-sided colitis and are used individually or in any combination for predicting mesalamine efficacy.

The one or more panels 108 preferably further comprises a fourth panel 124 identifying gender dependent target biomarkers 110 as shown and upon evaluation of the statistical analysis data (p values, t values, risk ratio, estimates and effect increments), were selected as being effective in predicting efficacy of mesalamine (2.4 g and 4.8 g daily therapy, given for six weeks) for female patients with proctosigmoiditis and are used individually or in any combination for predicting mesalamine efficacy.

The one or more panels 108 preferably further comprises a fifth panel 128 of gender dependent target biomarkers 110 as shown and upon evaluation of the statistical analysis data (p values, t values, risk ratio, estimates and effect increments), were selected as being effective in predicting efficacy of mesalamine (2.4 g and 4.8 g daily therapy, given for six weeks) for male patients with proctosigmoiditis and are used individually or in any combination to predict mesalamine efficacy.

It should be understood that one aspect of the subject invention provides a process and system whereby panels of gender dependent target biomarkers are used as for predicting mesalamine treatment outcomes on mild- to moderate UC patients with different colitis locations (left-sided colitis, proctosigmoiditis, pancolitis and extensive colitis). Such outcome predictions can be made by comparing the levels of such target biomarkers in patients with a reference to determine if the levels (quantity) of target biomarkers are higher or lower than the levels disclosed in the reference. Such differences are then used to create outcomes predicting the effectiveness of mesalamine treatment for the patient. Having now generally described the invention, the same will be more readily understood through reference to the following examples which are provided by way of illustration, are not intended to be limiting of the present invention, unless specified.

Exemplary Illustrations of Preferred Embodiments

A. Use of Mesalamine Non-Responder Serum (or Plasma) Biomarkers in Personalized UC Clinical Practice Using mesalamine to treat active UC is associated with clinical treatment fails in 60% of patients with moderate UC, compared to 80% treated with placebo. Due to the lack of understanding of disease pathophysiology, until now conventional mesalamine treatments did not take gender difference into consideration nor the locations of the disease within the colon. The panels of the subject invention operate to identify protein target biomarkers and use such target biomarkers to create outcomes with regard to mesalamine response for patients based on the patient's gender and anatomic colitis locations. Accordingly, the panels identifying specific target biomarkers operate to allow users to identify mesalamine non-responders earlier. Further, using such panels new clinical medication approaches are administered that have greater efficacy and alternative treatments for non-responders can be administered at an earlier stage of the disease.

By way of a non-limiting example, the subject invention provides outcomes that predict mesalamine responses on pancolitis and extensive colitis UC patients. Referring to FIGS. 1 and 2, in a preferred embodiment of the invention the process includes the step of identifying a patient that has been diagnosed as having UC (step 200). The colonic colitis location is then determined (step 202) such as by colonoscopy as part of standard clinic procedures. A clinician obtains one or more blood samples B (step 204) and creates a blood component 102 (step 206), such as in the form of a serum, as described above, and using the appropriate panel 108 identifies non-responder target biomarkers 110 as disclosed hereinabove (step 208), determines the levels (quantity) of the target biomarkers in the blood component 102 (step 210) prior to treatment of this patient's active colitis and compares the levels with levels of a reference 128 (step 212). Table 1 (FIGS. 4A and 4B) shows significant univariate analytes with a p value of less than 0.2 which were used to build the final biomarker multivariate model (reference) for success or failure of male/female pan/extensive colitis in Tables 2 and 3 (FIGS. 5 and 6, respectively). Table 1 also shows distribution of proteins that predict success or failure of 5ASA within subgroups. In Tables 2 and 3 the mean, standard error and range reported are reported in pg/ml, ng/ml, or the MFI ratio for each valid biomarker. N total indicates the total number of subjects within a subgroup with observations for each protein. MFI ratio unit indicates the ratio of median fluorescence intensity (MFI) of target-specific, antigen-coupled microspheres to MFI generated by a negative control microsphere tested in each sample well. The levels of the target biomarkers are then compared to prescribed levels of a reference 128 as shown in Tables 2 and 3 (FIGS. 5 and 6, respectively), (step 212) and an outcome 134 is generated (step 214). In a preferred embodiment of the invention the outcome predicts the efficacy of mesalamine (2.4 g and 4.8 g daily therapy, given for six weeks for female and male patients with pancolitis and extensive colitis). For example, if the patient shows significant difference in levels of the specified mesalamine non-responder target biomarkers (for example, higher serum level of IL13 at baseline with a 1 pg/ml increase) then the outcome 134 will show that it is likely that the patient will not respond to the mesalamine treatment. It should be understood that Table 2 (FIG. 5) identifies statistically predictive serological biomarkers consisting of serum proteins, autoimmune antibodies and antibodies recognizing infectious agents are shown for models of success vs. failure of 5ASA in each of the 5 subgroups. Effect increment indicates the quantitative increment of each protein in pg/ml, ng/ml, MFI ratio unit, or 5ASA dosage associated with the regression estimate and risk ratio. MFI ratio unit indicates the ratio of median fluorescence intensity (MFI) of target-specific, antigen-coupled microspheres to MFI generated by a negative control microsphere tested in each sample well. The values are stated in ng or pg/ml of protein as detected by the Rules-based medicine platform. It should also be understood that Table 1 (FIGS. 4A and 4B) shows significant univariate RBM analytes with a p value of less than 0.2 used for predictive multivariate modeling in male/female Pancolitis/Extensive.

In a preferred embodiment, in addition to the above mentioned panels of target biomarkers that are generic to both male and female pancolitis and extensive colitis patients, additional comparisons may be made using panels of additional target biomarkers, such as comparing levels of female specific target biomarker (CCL22, antibodies to Cholera toxin, *L. donovani*, HTCLV1/2 and autoantibody to HSP90 alpha) or levels of male specific target biomarkers may be used (IL1RN, CD40L, APOA1, PRL, IgA and autoantibody to HSP 71) as non-responder markers to determine if it is likely that this patient will not respond to mesalamine treatment. Consideration of an alternative drug therapy (such as anti-TNF molecules) is then made (step 216).

In another preferred embodiment of the invention as shown in Table 4 (FIG. 7), the subject invention provides a method and system for the prediction of mesalamine response on left-sided colitis UC female patients. Table 4 also shows significant univariate RBM analytes with p values of less than 0.2 used for multivariate and predictive modeling female left-sided colitis. In another non-limiting the method includes identifying a patient that has been diagnosed with left-sided colitis UC. Left-sided colitis is verified such as by colonoscopy as part of standard clinic procedures. It should be understood that for left-sided colitis, mesalamine is the common medication prescribed to the individual under current standard practice. Using the appropriate mesalamine non-responder target biomarkers identified hereinabove, a clinician runs one or more blood tests and obtains samples and creates a serum and identifies and determines the levels of one or more target biomarkers prior to treatment of the patient's active colitis. The levels of the target biomarkers are then be compared to levels or a reference, such as shown in Tables 2 and 3 (FIGS. 5 and 6, respectively), and an output is generated that predicts the efficacy of mesalamine (2.4 g and 4.8 g daily therapy, given for six weeks for male and female patients with left-sided colitis UC) is made. For example, if the patient shows significant difference in levels of the specified mesalamine non-responder target markers (for example MFI or protein level changes for antibody to *L. donovani*, Antibody to HTCLV1/2, HSP90alpha autoantibody for female patients with left-sided colitis, then a prediction is made that it is likely that the patient will or will not respond to the mesalamine treatment depending on the protein directionality outlined in Tables 2 and 3. Consideration of another drug therapy (such as anti-TNF molecules) could also be made at that time.

In another preferred embodiment of the invention, the subject invention includes a process and system for predicting mesalamine response on left-sided colitis UC male patients. Table 5 (FIG. 8) shows significant univariate analytes with p vales of less than 0.2, which were used to build the final biomarker multivariate model (reference) for success or failure of left-sided colitis UC male patients in Tables 2 and 3 (FIGS. 5 and 6, respectively). The process includes identifying a patient having UC, such as diagnosed with left-sided colitis UC. The condition and location are verified such as by colonoscopy as part of standard clinic procedures. It should be understood that for left-sided colitis, mesalamine is the common medication prescribed to the individual under current standard practice. Using the appropriate panel identifying mesalamine non-responder target biomarkers described hereinabove, a clinician runs one or more blood tests and obtains a blood sample using and creates a blood component, such as plasma or serum. The levels of the target biomarkers are determined prior to treatment of this patient's active colitis. The levels of the target biomarkers are compared to levels of a reference, such as shown in Tables 2 and 3 (FIGS. 5 and 6, respectively) and an outcome that predicts the efficacy of mesalamine, such as 2.4 g or 4.8 g daily therapy, given for six weeks for male and female patients with left-sided colitis UC, is made. For example, if the patient shows significant difference in levels of the specified mesalamine non-responder target markers (for example, MFI or protein level changes for antibody to *L. donovani*, Antibody to HTCLV1/2, HSP90alpha autoantibody for female patients and to HSP 71 autoantibody, IgA, APOA1 and PRL for male patients with left-sided colitis, then an outcome that predicts the likelihood that the patient will or will not respond to the mesalamine treatment is made depending on the protein directionality outlined in Tables 2 and 3. In a preferred embodiment the outcome further recommends an alternative drug therapy or regimen.

In another non-limiting example of the invention, the process and system operate to predict mesalamine response on proctosigmoiditis UC female patients is shown in Table 6 (FIG. 9). Table 6 also shows significant univariate analytes with p value of less than 0.2, which were used to build the final biomarker multivariate model (reference) for success or failure of proctosigmoiditis UC female patients in Tables 2 and 3 (FIGS. 5 and 6). The process includes identifying a patient that has been diagnosed with proctosigmoiditis UC. The proctosigmoiditis is verified such as by colonoscopy as part of standard clinic procedures. It should be understood that for proctosigmoiditis, mesalamine is the common medication prescribed to the individual in current standard practice. Using the appropriate mesalamine non-responder target biomarkers identified hereinabove, a clinician runs one or more blood tests and obtains a blood sample and creates a blood component, such as serum or plasma, and selects the proper panel and determines the levels of the target biomarkers prior to treatment of this patient's active proctosigmoiditis. The levels of the target biomarkers are then compared to levels of a reference, such as shown in Tables 2 and 3, and an outcome is generated that predicts the efficacy of mesalamine (such as for 2.4 g and 4.8 g daily therapy, given for six weeks for female and male patients with proctosigmoiditis). For example, if the patient shows significant difference in levels of the specified mesalamine non-responder target biomarkers (i.e. CCL22 and antibody to cholera toxin for females) then it is likely that the patient will not respond to the mesalamine treatment. In a preferred embodiment, the outcome includes an alternate drug therapy or regimen. Table 6 (FIG. 9) shows significant univariate analytes with a p value of less than 0.2, which were used to build the final biomarker multivariate model for success or failure of female proctosigmoiditis in Tables 2 and 3.

In another non-limiting example of the invention, as shown in Table 7 (FIG. 10), the subject invention is a process and system for predicting mesalamine response on male proctosigmoiditis UC patients. Table 7 also shows significant univariate analytes with p values of less than 0.2, which were used to build the final biomarker multivariate model (reference) for success or failure of proctosigmoiditis UC male patients in Table 2 and 3 (FIGS. 5 and 6, respectively). The process includes identifying a patient that has been diagnosed with proctosigmoiditis UC. The proctosigmoiditis is verified such as by colonoscopy as part of standard clinic procedures. It should be understood that for proctosigmoiditis, mesalamine is the common medication prescribed to the individual under current standard practice. Using the appropriate panel identifying mesalamine non-responder target biomarkers as described hereinabove, a clinician runs one or more blood tests and obtains a blood sample and creates a blood component, such as serum or plasma, and determines the levels of the target biomarkers prior to treatment of this patient's active proctosigmoiditis. The levels of the target biomarkers are then be compared to levels of a reference, such as shown in Tables 2 and 3 (FIGS. 5 and 6, respectively) and an outcome is generated that that predicts the efficacy of mesalamine (2.4 g and 4.8 g daily therapy, given for six weeks for male patients with proctosigmoiditis). For example, if the patient shows significant difference in levels of the specified mesalamine non-responder target biomarkers (for example, IL1RN, CD40L for males, then it is likely that the patient will or will not respond to the mesalamine treatment depending on the directionality of the protein test as listed in Table 3 (FIG. 6). Preferably, the outcome further includes an alternate drug therapy.

B. Use of Serum Target Biomarkers for Diagnosis and New Drug Development of Mild-to-Moderate UC Disease It should be understood that the target biomarkers identified in the panels are gender and colitis location specific UC disease target biomarkers. In another preferred embodiment of the invention, the panels are used for the early diagnosis of disease, localization of disease, the development of new personalized UC drugs, the measurement of the response to a drug treatment regimen or for assays for compound screening of therapeutics.

The following example illustrates the list of target biomarkers as shown in Tables 8-10 (FIGS. 11-13) for the male gender and Tables 11-13 (FIGS. 14-16) for the female gender that can be used for drug development, compound screening, diagnostics, location of disease and monitoring therapeutic responses. It should be understood to one skilled in the art that since pancolitis and extensive colitis at these colonic locations have a significantly greater risk of developing colon cancer than patients with disease limited to proctosigmotidis or left sided colitis, early diagnosis of the disease as well as effective therapeutics is highly desirable. The target biomarkers identified herein in Tables 8-10 (FIGS. 11-13) and Tables 11-13 (FIGS. 14-16) are gender and colitis location specific UC disease biomarkers that can be applied as targets of the early diagnosis of disease, for the development of new personalized UC drugs, further verification of disease location diagnosis, for the measurement of the response to drug therapy, or for assays for compound screening therapeutics.

Figure 17:
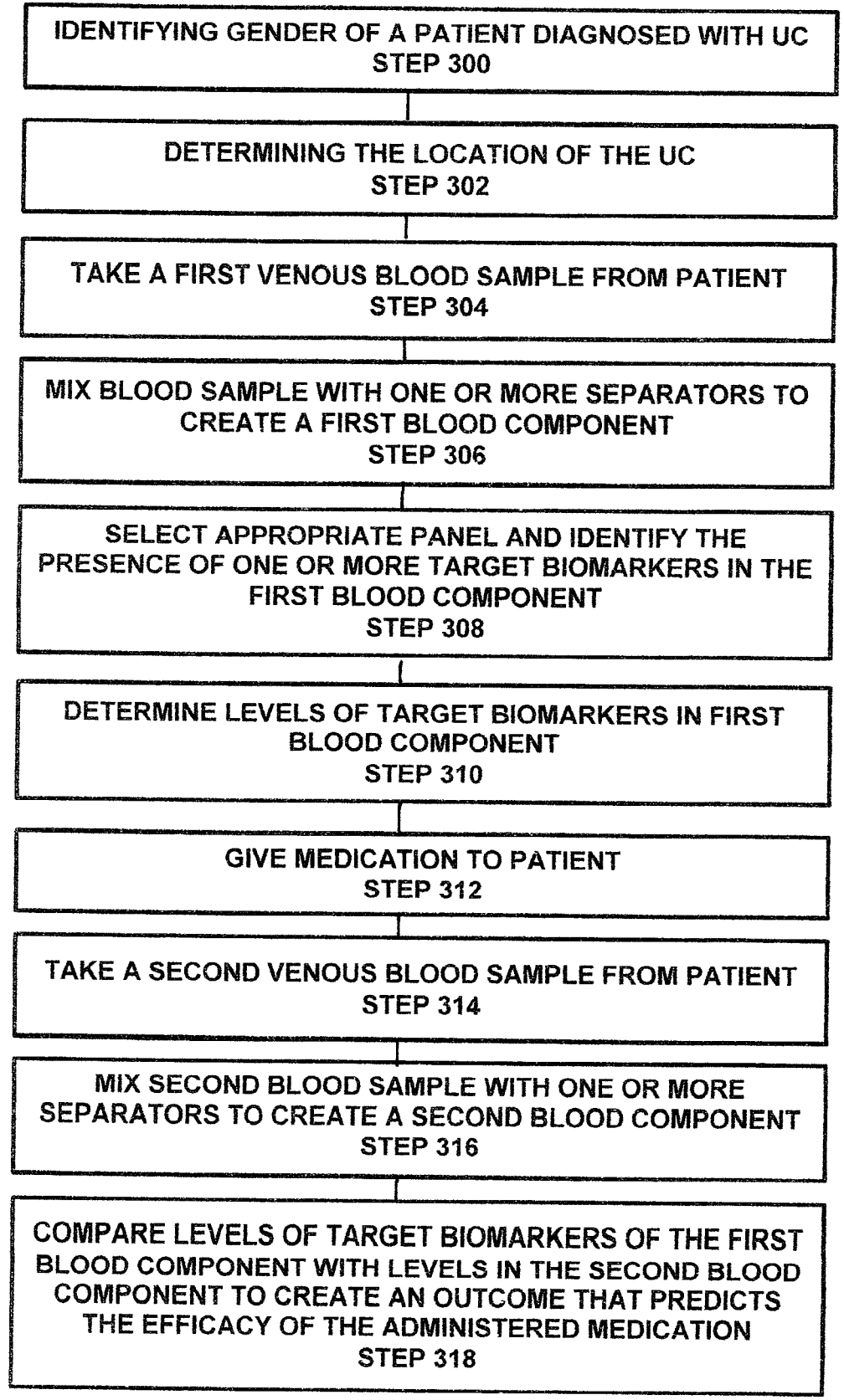
FIG. 17 is a flow diagram of the general methodology of a preferred embodiment of the invention showing the process of creating an outcome that predicts the efficiency of an administered medication.

In another preferred embodiment of the invention as shown in FIG. 17 the subject invention uses target biomarkers for patients with a particular UC condition. The subject invention provides a process whereby (such as in a non-limiting illustrative example, where the patient is diagnosed with pancolitis and extensive colitis) target biomarkers verify disease location and are used for drug targets, medication screening, diagnostics, and for monitoring therapeutic responses. In this particular example, the process includes identifying the gender of the patient that has been diagnosed with UC (step 300) and verifying the location of the UC such as by colonoscopy as part of standard clinic procedures (step 302). A clinician runs one or more blood tests and obtains a first blood sample (step 304) and creates a first blood component, such as a serum, by mixing the first blood sample with one or more separators (step 306). The appropriate panel for the patient's gender and UC is selected that identifies one or more target biomarkers (step 308) and the levels of the target biomarkers prior to treatment of this patient's UC, such as active left-sided colitis, is determined (step 310). Medication is then given to the patient (step 312). A clinician runs additional blood tests and obtains a second blood sample(s) (step 314) and creates a second blood component (step 316), such as a serum. The levels of the target biomarkers in the second blood component are then compared to levels of target biomarkers of a reference (step 318), such as for the particular colitis. In a preferred embodiment, as shown in FIG. 17, the reference comprises levels of the target biomarkers found in the first blood component.

In another non-limiting example, the reference comprises the levels of the target biomarkers shown in Tables 2 (FIG. 5) and 10 (FIG. 13) for male subject colitis and Tables 2 (FIG. 5) and 13 (FIG. 16) for female subject colitis. Depending on the changes in the levels of the target biomarkers (changes from levels found in the first blood component to levels found in the second blood component), an outcome is created (step 316) that predicts the efficacy of the administered medication. For example, if the patient shows significant difference in levels of the target biomarkers it can be determined that the proscribed medication is improving the patient's condition or is not effective for improving the patient's condition. It should now be apparent to one skilled in the art that the subject invention allows for the development of new personalized UC drugs, for the measurement and monitoring of a patient's response to drug therapy, or for assays for compound screening therapeutics.

In another non-limiting example the process includes identifying a male or female patient that has been diagnosed with left-sided colitis. The left-sided colitis is verified such as by colonoscopy as part of standard clinic procedures. A clinician runs one or more blood tests and obtains a first blood sample and creates a first blood component, such as a serum, and determines the levels of target biomarkers prior to treatment of this patient's active left-sided colitis. Medication is then given to the patient. A clinician runs additional blood tests and obtains an additional blood sample and creates a second blood component, such as a serum. The levels of the target biomarkers are then compared to levels of a reference, such as for an example as shown in Tables 2 (FIG. 5) and 10 (FIG. 13) for a male and Tables 2 (FIG. 5) and 13 (FIG. 16) for a female with pancolitis and extensive colitis and depending on the changes in the levels of the target biomarkers, an outcome can be created that predicts the efficacy of the administered medication. For example, if the patient shows significant difference in levels of the target biomarkers it can be determined that the proscribed medication is improving the patient's condition or not.

The following non-limiting example illustrates a list of target biomarkers for left-sided colitis, as shown in Table 8 (FIG. 11) for a male and shown in Table 11 (FIG. 14) for a female, that can be used for drug development, compound screening, diagnostics, and monitoring therapeutic responses. In a preferred embodiment the process includes identifying a patient that has been diagnosed with a particular UC, in this example left-sided colitis. The left-sided colitis is verified such as by colonoscopy as part of standard clinic procedures. A clinician runs one or more blood tests and obtains a blood sample and creates a blood component, such as a serum, and determines the levels of target biomarkers prior to treatment of this patient's active left-sided colitis. Medication is then given to the patient. A clinician obtains a second blood sample and creates a second blood component, such as a serum. The levels of the target biomarkers in the first blood component are then compared to levels of target biomarkers in the second blood component (reference), and depending on the changes in the levels of the target biomarkers, an outcome can be created that predicts as to the efficacy of the administered medication is made. For example, if the patient shows significant difference in levels of the target biomarkers it can be determined that the proscribed medication is improving the patient's condition or not.

The following non-limiting example illustrates the list of target biomarkers for proctosigmoiditis, such as shown in Table 9 (FIG. 12) for a male and Table 12 (FIG. 15) for females, that can be used for drug development, compound screening, diagnostics, and monitoring therapeutic responses. In a preferred embodiment the process includes identifying a particular UC condition. In this illustrative example the patient has been diagnosed with proctosigmoiditis. The proctosigmoiditis is verified such as by colonoscopy as part of standard clinic procedures. A clinician runs one or more blood tests and obtains a first blood sample and creates a blood component, such as a serum, and determines the levels of target biomarkers prior to treatment of this patient's active proctosigmoiditis. Medication is then given to the patient. A clinician runs additional blood tests and obtains a second blood sample and creates a blood component, such as a serum. The levels of the target biomarkers in the first blood component are then compared to levels of the second blood component (reference), and depending on the changes in the levels of the target biomarkers, an outcome can be created that predicts the efficacy of the administered medication. For example, if the patient shows significant difference in levels of the target biomarkers it can be determined that the prescribed medication is improving the patient's condition or not.

It should now be apparent to one skilled in the art that the present invention provides a process and system whereby panels of target biomarkers are used for risk assessment and predict with a high degree of reliability the treatment outcome with respect to a patient expressing higher than normal levels of targeted biomarkers and thus provides substantive value in various aspects of patient care management. It should also now be apparent to one skilled in the art that the process and system of the subject invention prevents or reduces the likelihood of treatment using ineffective medications as well as reducing the possibility of the patient experiencing un-necessary side effects of mesalamine as well as the potential delay in clinical recovery due to use of ineffective drug choice. Further, it should be understood that the process and system reduce a delay in in clinical recovery that could be clinically significant since pancolitis patients have great risk in developing colon cancer. Accordingly, the use of the process and system (of personalized medicine for patients with UC) of the subject invention is very beneficial to the patient, the prescribing practitioner, and insurance companies.

Figure 18:
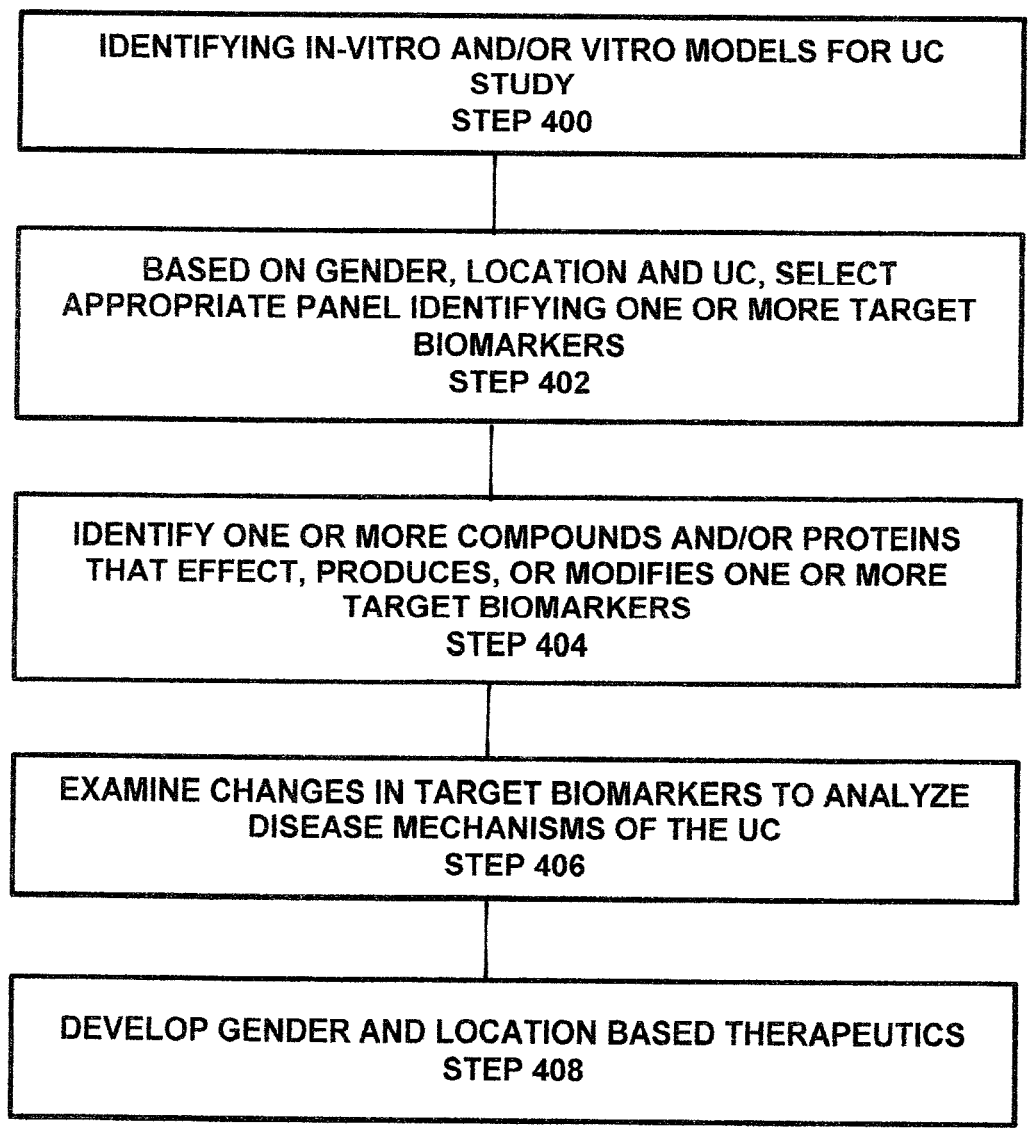
FIG. 18 is a flow diagram of the general methodology of a preferred embodiment of the invention showing the process used for drug development, compound screening, diagnostics and monitoring therapeutic responses using the system of the subject invention.

It should now be understood that the panels of target biomarkers identified for the specific UC conditions and in conjunction with other clinical factors, is used to tailor treatments for individual patients including selecting specific drug treatments and administration regimes, as well used for developing treatments, therapies and medications. In a preferred embodiment, as shown in FIG. 18, the system and process of the subject invention further comprises the steps of identifying in-vitro (cell based) and/or in vivo (animal) models for UC study (step 400). It should be understood that as used herein models can be individual (patient) or animal subjects for use in the study. For a particular gender and UC, the appropriate panel identifying one or more target biomarkers is selected (step 402). One or more compounds and/or proteins that effect, produces, or modifies the one or more target biomarkers are identified (step 404) using standard procedures. Utilizing the changes in the one or more target biomarkers caused by the one or more compounds and/or proteins, disease mechanisms of the UC are analyzed (step 406). It should now be apparent to one skilled in the art that the changes to the identified target biomarkers caused by various compounds and/or proteins permits the creation of new, safe, effective and gender and location-based therapeutics to be developed (step 408). For example, in a non-limiting illustration medications can be conventionally developed that modifies levels of target biomarkers in a blood component created from a blood sample from a model suffering from UC until such levels fall within a range of prescribed levels of target biomarkers. In another non-limiting illustration, after medication has been administered to the model and given time to react, the levels of the target biomarkers in a blood component created after treatment are compared to levels of the target biomarkers in a blood component created prior to treatment and the effectiveness of the new drug therapy is determined. For example, if the treatment alters one or more of the target biomarkers the efficacy of the administered medication can be determined and if the treatment is not effective, changes can be made to the therapy. If the model shows significant difference in levels of the target biomarkers it can be determined that the proscribed medication is improving the model's condition or is not effective in improving the model's condition. Using the process and system of the subject invention effective dosage of the medication can also be conventionally determined.

Accordingly, the process and system of the subject invention is directed to a more effective, individual (personalized-medicine) based treatment regimen which is built on panels of clinical identified biomarkers. It should now be apparent that the process and system of the subject invention provides an accurate and easy to administer process that can be used for the diagnosis, prognosis, and therapy alternatives for the treatment of UC. In a preferred embodiment of the invention the process of system of the subject invention provides means whereby panels identifying target biomarkers operate as drug targets that are conventionally used to develop new medications and therapies effective for the treatment of UC patients. For example, if a patient shows significant difference in levels of the target biomarkers it can be determined that the proscribed medication is improving or not improving the patient's condition.

In another preferred embodiment of the invention the process and system use panels of target biomarkers as a screening mechanism to conventionally identify therapeutic compounds that may have a therapeutic benefit and potential use for medications to treat UC patients. For example, by examining target biomarkers for a particular UC condition, compounds and/or proteins can be identified that are known to effect, produce, modify, or change one or more of the target biomarkers. Such compounds and/or proteins can then be used to create medications for that particular UC condition.

In another preferred embodiment of the invention, the process and system use panels of target biomarkers such that by comparing changes in the level of one or more of the target markers, as described above, therapeutic effectiveness of medications can be administered to UC patients.

In another preferred embodiment of the invention the process and system of the subject invention operates to identify additional proteins, both upstream and downstream, of the disease pathway for a particular UC condition. Such proteins are then used as additional target biomarkers for creating medications for the particular UC condition. Further, after such proteins are identified changes therein (and their effect on target biomarkers) are determined, such information is used to provide insight into the disease mechanism of the particular UC condition.

In another preferred embodiment of the invention, the process and system of subject invention uses panels of target biomarkers to monitor the therapeutic efficacy of the medication being administered to a UC patient.

Although the foregoing invention has been described in some detail for purposes of clarity of understandings, it will be apparent that certain changes and modifications may be practiced within the scope of the appended claims. It should now be apparent that the various embodiments presented can be easily modified while keeping within the scope and spirit of the subject invention. Accordingly, it should be understood that the present disclosure is to be considered as exemplary of the principals of the invention and is not intended to limit the invention to the embodiments and the specific examples illustrated and the invention is not to be limited to the details given herein, but may be modified within the scope and equivalents of the descriptions and examples contained herein.

The invention claimed is:

1. A process for the treatment of ulcerative colitis (UC), the process comprises the steps of:
    identifying a patient diagnosed with UC;
    identifying if the patient is a male or female;
    determining the location of the UC;
    obtaining a first blood sample from the patient;
    selecting a panel of target biomarkers based on the location of the UC and if the patient is a male or female;
    making a determination of the existence and level of the one or more of the identified target biomarkers in the first blood sample;
    using the determination of the existence and the level of the one or more target biomarkers in the selected panel to make a prediction as to the efficacy of administering mesalamine treatment to the patient and using the prediction select a treatment whereby mesalamine is administered to the patient or a treatment whereby an alternate treatment is administered to the patient for treating the ulcerative colitis and the selected treatment is administered to the patient for the UC;
    after administering the selected treatment to the patient, obtaining a second blood sample from the patient;
    determining the level of each of the one or more target biomarkers in the selected panel in the second blood sample;
    making a second comparison of the levels of the one or more target biomarkers in the second blood sample with the levels of the one or more target biomarkers in the first blood sample; and
    using the second comparison to evaluate the effectiveness of the selected treatment and using the evaluation of the effectiveness of the selected treatment continue with the selected treatment or administer another treatment effective for the treatment of UC;
    wherein the identified target biomarkers in the panel for a male or female patient having pancolitis and extensive UC are GSTM1, IL13, RETN and Histone H2a autoantibody;
    wherein the identified target biomarkers in the panel for a female having left sided UC are antibody to *L. donovani*, HTCLV1/2 and HSP90alpha autoantibody;
    wherein the identified target biomarkers in the panel for a male patient having left sided UC are APOA1, PRL, HSP 71 autoantibody and IgA;
    wherein the identified target biomarkers in the panel for a female patient having proctosigmoiditis UC are CCL22 and antibody to cholera toxin; and
    wherein the identified target biomarkers in the panel for a male patient having proctosigmoiditis are ILRN and CD40 LG.

2. The process of claim 1 wherein the first and second blood samples are mixed with one or more separators to devoid the first and second blood samples of red and white blood cells.

3. The process of claim 2 wherein the one or more separators are anticoagulants.

4. A process of claim 1 further comprising the steps of:
    identifying one or more compounds or proteins that effect, produce or modify the one or more of the identified target biomarkers; and
    wherein the treatment is based on one or more of the identified compounds or proteins.

5. The process of claim 4 further comprising the steps of identifying changes in one or more of the target biomarkers caused by one or more compounds or proteins and using the identified changes to analyze the disease mechanism of the UC.

6. A process for the treatment of ulcerative colitis (UC), the process comprises the steps of:
    identifying a patient diagnosed with UC;
    identifying if the patient is male or female;
    determining the location of the UC;
    obtaining a first blood sample from the patient;
    selecting a panel of target biomarkers based on the location of the UC and if the patient is male or female, wherein the target biomarkers indicate the efficacy of mesalamine for treating the patient;
    making a determination of the efficacy of mesalamine for treating the patient using the existence and level of the one or more of the target biomarkers in the selected panel in the first blood sample;
    using the determination either administer a mesalamine treatment to the patient or administer an alternate treatment used to treat a patient having UC;
    wherein the identified target biomarkers in the panel for a male or female patient having pancolitis and extensive UC are GSTM1, IL13, RETN and Histone H2a autoantibody;
    wherein the identified target biomarkers in the panel for a female having left sided UC are antibody to *L. donovani*, HTCLV1/2 and HSP90alpha autoantibody;
    wherein the identified target biomarkers in the panel for a male patient having left sided UC are APOA1, PRL, HSP 71 autoantibody and IgA;
    wherein the identified target biomarkers in the panel for a female patient having proctosigmoiditis UC are CCL22 and antibody to cholera toxin; and
    wherein the identified target biomarkers in the panel for a male patient having proctosigmoiditis are ILRN and CD40 LG.

* * * * *